(12) United States Patent
Umeda et al.

(10) Patent No.: US 8,257,771 B2
(45) Date of Patent: Sep. 4, 2012

(54) INNOVATIVE PASTEURIZATION METHOD, USE THEREOF AND APPARATUS

(75) Inventors: Keiji Umeda, Tokyo (JP); Yositaka Nadachi, Tokyo (JP); Hiromu Shishido, Hiroshima (JP); Ryo Maruyama, Hokkaido (JP); Yukio Ogasawara, Hokkaido (JP); Takumi Yamamoto, Hokkaido (JP); Seiichiro Isobe, Ibaraki (JP)

(73) Assignees: Umeda Jimusho Ltd., Machida-shi (JP); National Agriculture and Food Research Organization, Tsukuba-shi (JP); Taiyo Seisakusho Co., Ltd., Hokuto-shi (JP)

( * ) Notice: Subject to any disclaimer, the term of this patent is extended or adjusted under 35 U.S.C. 154(b) by 843 days.

(21) Appl. No.: 11/632,483

(22) PCT Filed: Jul. 19, 2005

(86) PCT No.: PCT/JP2005/013264
§ 371 (c)(1),
(2), (4) Date: Feb. 15, 2007

(87) PCT Pub. No.: WO2006/009150
PCT Pub. Date: Jan. 26, 2006

(65) Prior Publication Data
US 2008/0020114 A1  Jan. 24, 2008

(30) Foreign Application Priority Data

Jul. 16, 2004 (JP) ................................. 2004-210872

(51) Int. Cl.
*A23L 1/00* (2006.01)

(52) U.S. Cl. ........ 426/511; 426/510; 426/506; 426/407; 426/520; 422/1; 422/26; 422/28

(58) Field of Classification Search .................. 426/665, 426/506, 511, 407, 520, 521, 510; 99/324, 99/330, 331; 422/1, 26, 28
See application file for complete search history.

(56) References Cited

U.S. PATENT DOCUMENTS

| | | | | | |
|---|---|---|---|---|---|
| 2,141,591 | A | * | 12/1938 | Bonner | 126/20.1 |
| 2,909,985 | A | * | 10/1959 | Abrams | 99/453 |
| 3,673,386 | A | * | 6/1972 | Drugmand et al. | 219/523 |

(Continued)

FOREIGN PATENT DOCUMENTS

JP        6 90677        4/1994

(Continued)

*Primary Examiner* — Viren Thakur
*Assistant Examiner* — Preston Smith
(74) *Attorney, Agent, or Firm* — Oblon, Spivak, McClelland, Maier & Neustadt, L.L.P.

(57) ABSTRACT

A method for heating and pasteurizing a material, comprising placing the material inside of a semi-sealed chamber at atmospheric pressure that contains an atmosphere produced by replacing air in the chamber with a gas component produced by spraying or injecting hot water droplets and steam at a temperature of at least 100° C. into the chamber which is heated to a temperature of at least 100° C. which is equal to or higher than the temperature of the sprayed hot water droplets and steam, which gas component has a humidity of at least 95% and contains no more than 1% oxygen; contacting said material to the gas component for exposing it to continual temperature variation during heating ranging from 10-50° C. inside the chamber at temperature(s) ranging from 90-180° C. for a time sufficient to heat or pasteurize it. An apparatus for performing this method.

11 Claims, 17 Drawing Sheets

U.S. PATENT DOCUMENTS

| | | | |
|---|---|---|---|
| 4,263,258 A * | 4/1981 | Kalasek | 422/113 |
| 5,619,983 A * | 4/1997 | Smith | 126/348 |
| 5,824,266 A * | 10/1998 | Badertscher et al. | 422/26 |
| 5,870,975 A * | 2/1999 | Luc | 122/39 |
| 6,183,798 B1 * | 2/2001 | Ishii | 426/507 |
| 6,582,743 B2 * | 6/2003 | Cai | 426/510 |
| 2003/0054079 A1 * | 3/2003 | Reaves et al. | 426/511 |

FOREIGN PATENT DOCUMENTS

| | | |
|---|---|---|
| JP | 2001 61655 | 3/2001 |
| JP | 2001214177 | 8/2001 |
| JP | 2001 263668 | 9/2001 |
| JP | 2001 323085 | 11/2001 |
| JP | 2002 194362 | 7/2002 |
| JP | 2004 332956 | 11/2004 |

* cited by examiner

INNOVATIVE PASTEURIZATION METHOD, USE THEREOF AND APPARATUS

TECHNICAL FIELD

The present invention relates to a method of heating and pasteurizing that uses water in gas form (gaseous water) and to an apparatus therefor. More particularly, the present invention relates to a method of heating and pasteurizing using gaseous water in which a material to be treated is heated in a gaseous water atmosphere formed by substituting the interior of a heating chamber with gaseous water. The present invention also relates to a method of producing heated/pasteurized products using the aforementioned method of heating and pasteurization and to an apparatus for heating and pasteurizing with gaseous water for use in the aforementioned method.

BACKGROUND ART

With regard at a general level to heating methods that use steam for heating, for example, the use of saturated steam or so-called steam heating (steaming) and high-pressure steam heating using high-pressure steam generated from a boiler are known; also known is superheated steam heating, which uses high-temperature, high-pressure superheated water vapor (superheated steam) that is produced when high-pressure steam generated from a boiler is additionally heated to high temperatures. Among these, steam heating is a method in which the material to be treated is subjected to heat treatment by so-called "steaming", in which a heating chamber is filled with steam produced by heating water to about 100 to 120° C. High-pressure steam heating using high-pressure steam from a boiler is a method in which the material to be treated is subjected to heat treatment using as the heat source saturated steam that has been pressurized and brought to a higher temperature.

Superheated steam heating, on the other hand, is a method in which high-pressure steam produced from a boiler is additionally heated to a higher temperature of at least 140° C., yielding a thermal energetically quasi-stable superheated steam, which is injected into a heating chamber to fill same and thereby subject the material to be treated to heat treatment. Since a dry high-temperature, high-pressure atmosphere is formed by the superheated steam in this method, this heating method is used as a heating means that approximates baking. Since superheated steam heating can employ a high-temperature, high-pressure, high-caloric, and thermal energetically quasi-stable dry steam, a broad range of applied technology has been proposed for superheated steam heating in the form of, for example, means for heating and baking food products, means for roasting wastes from the agricultural and livestock industries, means for the carbonization of, for example, wood, and means for cleaning, for example, metal surfaces (Japanese Patent Application Laid-open Numbers Hei 06-090677, 2001-061655, 2001-214177, 2001-323085, and 2002-194362).

However, this type of heating method suffers from a number of problems, for example, a boiler is required to generate high-pressure, high-temperature steam and a high-temperature heating means is required to subject the high-temperature, high-pressure steam from the boiler to additional heating; the facility scale is large; a large energy loss is incurred in order to inject the high-temperature, high-pressure superheated steam into the heating chamber, yielding a lower efficiency than in established baking methods; so-called ordinary steam heating is satisfactory in many cases, so there is presumably little requirement for the utilization of superheated steam heating; this type of method is unsuitable for small runs; and, since the baking effect has yet to be thoroughly identified, there is some distance to go in order to realize practical application. Moreover, these problems have yet to be solved.

DISCLOSURE OF THE INVENTION

Against this background and in view of the prior art described above, the present inventors carried out intensive and extensive investigations in order to develop an entirely novel steam-based method of heating and pasteurizing that would be distinct from the ordinary steam heating described above and the superheated steam heating described above. As a result of these investigations, the present inventors discovered that the characteristics of water in gas form are not necessarily thoroughly exploited by the prior-art methods; that the characteristics of water in gas form can be thoroughly exploited by substituting the interior of a heating chamber with water in gas form to form a "gaseous water" atmosphere; and that this enables the realization of a novel steam-utilizing method of heating and pasteurizing that is essentially different from the prior-art methods.

An object of the present invention is to provide a novel method of heating and pasteurizing that uses "gaseous water" and that is entirely distinct from the existing steam heating and superheated steam heating.

Additional objects of the present invention are to provide an apparatus that produces "gaseous water" that can be used by the aforementioned "gaseous water" heating and pasteurizing method and to provide an apparatus for heating and pasteurizing using "gaseous water".

Other objects of the present invention are to provide a method that forms a gas component (gaseous water) by substituting the interior of a heating chamber with water in gas form wherein this gas component has a humidity of at least 99.0% and an oxygen concentration no greater than 1.0%; to provide a method of heating and pasteurizing a material to be treated using the "gaseous water" atmosphere formed by the method just described; to provide a method of producing a product that has been heated and pasteurized by the method just described; and to provide an apparatus therefor.

The present invention comprises the following technical means in order to achieve the objects cited above.

(1) A method of heating and pasteurizing a material to be treated, comprising the steps of:
1) continuously injecting hot water heated to at least 100° C. and/or steam into a heating chamber comprising a semi-sealed space and heated to at least the same temperature as the hot water and/or steam, to form water microdroplets and moist hot steam;
2) replacing air within the heating chamber with the water microdroplets and moist hot steam to effect filling with a gas component that has a composition of at least 95% humidity and an oxygen concentration not greater than 1% and that is maintained in a temperature range of 90 to 180° C.; and
3) carrying out a heating and pasteurizing treatment by effecting, with the water microdroplets and the moist hot steam, continuous amplitude heating at a temperature difference of at least 10° C. in the temperature range on a material to be heated and pasteurized.

(2) The method of heating and pasteurizing according to (1), wherein the air within the heating chamber is replaced with the water microdroplets and moist hot steam to effect filling with a gas component that has a composition of at least 99% humidity and an oxygen concentration not greater than 1% and that is maintained in the temperature range of 95 to 150° C.

(3) The method of heating and pasteurizing according to (1), wherein water microdroplets and moist hot steam, and dry hot steam, are generated by controlling the temperature of the hot water and/or steam and the temperature within the heating chamber comprising a semi-sealed space, and the material to be treated is subjected to a heating and pasteurization treatment by any combination of these three species.

(4) A method of producing a heated and pasteurized product, by
producing a heated and pasteurized product by heating and pasteurizing a material to be treated with any one of the heating and pasteurizing methods according to (1) to (3).

(5) The method of producing a heated and pasteurized product according to (4), wherein the material to be treated is a food or food ingredient.

(6) An apparatus for heating and pasteurizing with gaseous water used in the method according to any one of (1) to (5), comprising as constituent elements at least:
a heating chamber with a semi-sealed configuration, that heats a material to be treated while isolating the material to be treated from the outside atmosphere;
heating means that heats the heating chamber to a prescribed temperature exceeding 100° C.; and
a steam-generating means that continuously injects hot water heated to at least 100° C. and/or steam into the heating chamber, thereby generating water microdroplets and moist hot steam and transporting same in a prescribed direction, wherein
heating and pasteurization are carried out by continuously injecting hot water heated to at least 100° C. and/or steam into the heating chamber, thereby generating water microdroplets and moist hot steam, and filling the interior of the heating chamber with steam and water microdroplets as such in an atmospheric pressure state, replacing air in the interior of the heating chamber with a gas component that has a composition of at least 95% humidity and an oxygen concentration of not more than 1.0% and that is maintained in a temperature range of 90 to 180° C., and effecting, with the water microdroplets and moist hot steam, continuous amplitude heating at a temperature difference of at least 10° C. in the temperature range on the material to be treated within the heating chamber.

(7) The apparatus for heating and pasteurizing according to (6), wherein the apparatus comprising, as the steam-generating means, a feed water tank, a feed water pump that feeds water from the feed water tank to the heating chamber, a feed water capillary that is provided with an external heater in order to heat the supplied water to at least 100° C., a spray nozzle disposed at the tip of the feed water capillary, and a rotatable circulation fan that can microfine-size the high-temperature steam sprayed from the injection nozzle and that is capable of transporting the high-temperature steam in a prescribed direction.

(8) The apparatus for heating and pasteurizing according to (6), wherein the apparatus comprising, as the heating means that heats the heating chamber to a prescribed temperature above 100° C., a plurality of sheath heaters disposed in a hairpin configuration in a position in contact with the water microdroplets and moist hot steam generated within the heating chamber.

Figure 1:
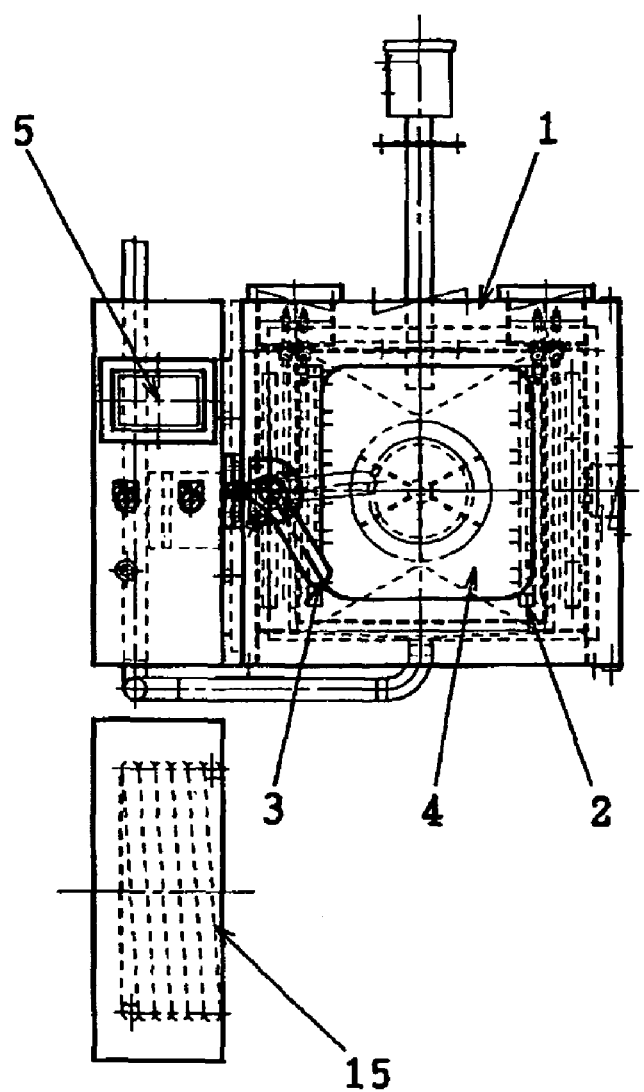
FIG. 1 is a front elevation of an example of an apparatus according to the present invention.

The present invention is explained in additional detail hereinbelow.

The heating and pasteurizing method according to the present invention ("heating and pasteurizing" are in some instances referred to below simply as "heating") comprises (1) continuously injecting hot water heated to at least 100° C. and/or steam into a heating chamber comprising a semi-sealed space and heated to at least the same temperature as the hot water and/or steam, to form water microdroplets and moist hot steam; (2) replacing the air within the heating chamber with the water microdroplets and moist hot steam to effect filling with a gas component that has a composition of at least 95% humidity and an oxygen concentration no greater than 1% and that is maintained in the temperature range of 90 to 180° C.; and (3) carrying out a heat treatment by effecting, with the water microdroplets and the moist hot steam, continuous amplitude heating at a temperature difference of at least 10° C. in the aforementioned range on a material to be treated. The water microdroplets and moist hot steam of the present invention denote a mixed system of high-humidity moist hot steam and water microdroplets that are produced locally by the condensation of this steam, while dry hot steam denotes high-dryness steam that is produced locally by the drying of the moist hot steam. The present invention comprises carrying out a heat treatment by effecting, with the water microdroplets and the moist hot steam, continuous amplitude heating at a temperature difference of at least 10° C. in the temperature range of 90 to 180° C. on a material to be treated. As used herein, this continuous amplitude heating at a temperature difference of at least 10° C. denotes continuous heating, in the temperature range of 90 to 180° C., at an amplitude for the temperature difference that exceeds 10° C. in a short period of time. For example, a material to be treated can be continuously heated in the present invention at an amplitude for the temperature difference of 10 to 50° C. The aforementioned mixed state of water microdroplets and moist hot steam is called gaseous water (Aqua-gas®) in the present invention.

A material to be heated is heated in the present invention both by heating the heating chamber to a prescribed temperature in excess of 100° C. and by a gaseous water atmosphere formed by introducing hot water and/or steam into the heating chamber and substituting the interior of the heating chamber with water in gas form (gaseous water), thereby reducing the oxygen concentration to 1.0% or less. The heating chamber in the present invention comprises a prescribed semi-enclosed space capable of heating the material to be heated while isolating the material to be heated from the outside atmosphere, and a suitable example is a semi-sealed space having a plate for mounting the material to be heated and an openable/closable door, part of which is formed as a glass window. The heating chamber is suitably constructed of stainless steel material. The heating chamber is heated to a prescribed temperature in excess of 100° C. in the present invention, but in this case is suitably heated to a temperature that is equal to or greater than the temperature of the hot water and/or steam that is introduced into the heating chamber.

As cited above, in the present invention the heating chamber is heated to a prescribed temperature and water microdroplets and moist hot steam are generated at the heating chamber to thereby replace the air within the heating chamber with water in gas form. To form the water microdroplets and moist hot steam in this case, for example, water being transported through a capillary at a prescribed flow velocity is heated with a heater from outside the capillary and is then introduced into the heating chamber through a nozzle disposed at the end of the capillary. The water microdroplets and moist hot steam constitute a high-temperature, atmospheric-pressure gas component heated to 100 to 180° C. and more suitably to 95 to 150° C. and function to heat the material to be treated at a high energy efficiency. The heated water is sprayed through the nozzle into the heating chamber. Since the interior of the heating compartment is thermally controlled to a prescribed temperature of at least 100° C. under atmospheric pressure conditions, the sprayed water droplets evaporate, yielding a water microdroplet+moist hot steam mixed state within the heating chamber. By adjusting the quantity of water sprayed and the water droplet size at this point, a state can be elaborated in which water microdroplets are locally mixed in a steam atmosphere; such a state is denoted as Aqua-gas.

In the present invention, the water in the feed water tank is pumped up by the feed water pump, fed through a conduit comprising a capillary into a steam-generating heat-accumulating panel, heated by a heater to a prescribed temperature, for example, 105 to 200° C., and as such is ejected at high velocity as hot water and/or steam from a steam injection nozzle disposed at the end of the capillary. In this case, the steam nozzle is suitably selected from steam nozzles that have microfine ejection openings formed at the terminus and that are capable of ejecting the hot water and/or steam while microfine-sizing same. The size, number, pattern, and so forth of these microfine ejection openings can be freely selected. The ejection velocity of the hot water and/or steam from the steam injection nozzle is suitably about 160 to 200/s at the tip of the injection nozzle; however, this ejection velocity is not limited to these values and can be freely set, for example, by changing the size and number of the microfine ejection openings, in correspondence to, for example, the size and type of the apparatus and its intended use.

The formation of a gaseous water atmosphere in the heating chamber can be carried out in the present invention, for example, by introducing steam ejected from the aforementioned microfine injection nozzle into the heating chamber with the steam being injected into a circulation fan that is disposed in the vicinity of the terminus of the injection nozzle, wherein the steam is transported in a prescribed flow direction by the impingement force and drafting force due to the rotation of the circulation fan; by bringing the steam into contact with a heater disposed in conformity with this flow direction in order to introduce the steam throughout the entire heating chamber without a drop in the temperature of the steam; and by substituting the interior of the heating chamber with water in gas form maintained at a prescribed temperature to fill the heating chamber with a gas component having at least 95% humidity and no more than a 1.0% oxygen concentration and more suitably a humidity of at least 99.0% and no more than a 1.0% oxygen concentration. The hot water and/or steam injected from the microfine ejection openings are subjected to an additional size reduction by impact on the circulation fan. In addition, the heater disposed downstream in the flow direction set up by the circulation fan is disposed in a position and direction such that its surface comes into direct contact with the injected hot water and/or steam over a broad area and suitably interfaces with the injected hot water and/or steam as much as possible. This enables the heater to transfer heat to the hot water and/or steam with good efficiency and thereby makes it possible to reliably prevent a drop in the temperature of the injected hot water and/or steam.

This circulation fan can be disposed, for example, in the center of the back side of the interior of the heating chamber and can be exemplified by a circulation fan that has the capacity to transport the injected hot water and/or steam in such a manner that the hot water and/or steam comes into direct contact with heaters disposed within ducts positioned on the left and right sides within the heating chamber; however, the circulation fan is not limited to the preceding. The heater can be very suitably exemplified by a plurality of, for example, sheath heaters disposed in a hairpin configuration so as to increase the surface area of contact with the injected hot water and/or steam. The heater, however, is not limited to the preceding, and any heater having the same functionality can be similarly used. The rotation rate and direction of rotation of the circulation fan are set in such a manner that the injected hot water and/or steam can be circulated as a circulating flow within the ducts, taking into consideration the size of the apparatus, the position and shape of the ducts, the shape and installed position of the heater, and so forth.

Utilizing the aforementioned gaseous water as a heating medium, the heating chamber carries out a prescribed heat treatment by introducing the material to be treated into the heating chamber in a stage in which substitution by gaseous water has been carried out. The heat treatment referred to here encompasses any type of heat treatment that utilizes the aforementioned gaseous water as a heat source and is appropriately exemplified by the thawing of frozen materials by heating, the thermal processing of materials, the drying of materials by heating, the melting or baking of materials by heating, the thermal processing of water-containing liquids, and so forth. There are no particular limitations on the material to be treated according to the present invention, and the material to be treated can be suitably exemplified by frozen products, plant products, organic materials, inorganic materials, agricultural products, food ingredients, wood, metals, ceramics, plastics, and so forth. The present invention, however, is not limited to the preceding and otherwise can be applied to any type of material to be treated to which a heat treatment, such as drying, heating, pasteurization, baking, thawing, cooking, and so forth, is applied.

After the prescribed heat treatment has been carried out, the material to be treated residing in the heating chamber is removed from the heating chamber according to a suitable timing and the gaseous water that has come into contact with the material to be treated is discharged from the system through a gaseous water exhaust outlet. The hot water and/or steam injected into the heating chamber first impinges on the circulation fan and is thereby subjected to microfine-sizing and is transported into a duct; it comes into contact with a heater disposed in the duct and is heated to a prescribed temperature; and it then comes into contact with the material to be treated that has been introduced into the heating chamber and is utilized as a heating medium and is thereafter discharged from the system. While the thermal energy of the gaseous water acting as a heating medium is utilized as a heat source for subjecting the material to be treated to a heat treatment, in the present invention, the injected hot water and/or steam is not brought into contact as such with the material to be treated; rather, it is brought into contact with the material to be treated after heating by the heater disposed in the duct. This enables the material to be treated to be subjected to a highly efficient heating since the material to be treated is heated without a decline in the heat content of the injected hot water and/or steam.

In addition, heat having a high heat transfer rate can be continuously transferred into the interior of the material to be treated and the gaseous water can infiltrate into the interior of the material to be treated at good efficiencies and can rapidly heat the material to be treated, because the injected hot water and/or steam, for example, is additionally heated with a heater and is subjected to an additional microfine-sizing due to its high-velocity impingement on the circulation fan and subdivision of the water droplets by the impact due to this impingement to give a microfine-sized, high-temperature gaseous water that exhibits a high capacity to infiltrate into the interior of the material to be treated and that comprises high-temperature, high-thermal conductivity water particles that are completely transparent by visual inspection, and because the follow-on high-temperature gaseous water constantly feeds thermal energy to the gaseous water that has already infiltrated into the interior of the material to be treated and that has already participated in heat exchange.

The water droplets of ejected hot water and/or steam are, as necessary, additionally microfine-sized by impingement on the circulation fan and are filled into the heating chamber as microfine water particles with a pasteurizing activity. According to the results of experiments, the pH of the water taken from the feed tank was about 6.9 to 7.1, while the pH of these pasteurizing microfine water particles is about 5.2 to 5.8, resulting in the formation, in cooperation with the high temperatures of at least 105° C., of a strongly pasteurizing gaseous water atmosphere in the heating chamber. Accordingly, when the present invention is applied to, for example, agricultural products or food ingredients, a strong pasteurizing effect can be applied at the same time as heating since the material to be treated can be heat treated under a highly pasteurizing atmosphere.

An embodiment of the gaseous water-based heating apparatus according to the present invention is specifically described below based on the drawings. However, while an example of the apparatus according to the present invention is shown in the drawings, the present invention is not limited to this. Moreover, the individual constituent elements can be replaced by similar means that exhibit a similar function, and any known means can be additionally attached. FIG. 1 is a front elevation of a heating apparatus according to the present invention and shows a batch-type apparatus comprising the following as constituent elements: a heating chamber 1 for isolating the material to be treated from the outside atmosphere and heating this material while it is in this isolated condition, an openable/closable door 2 disposed at the front of the heating chamber 1, a handle 3 on the door 2 and a window 4 in the door 2, an operating panel 5, and an apparatus 15 for heating the feed water. The heating chamber 1 forms a prescribed space that can hold the material to be treated (not shown) in its interior and that can heat same. The door 2 disposed on the front of the heating chamber 1 has a structure that enables it be opened and closed as appropriate by the operation of the handle 3, while the window 4 is provided to enable confirmation of the heating status of the material to be treated. A single heating chamber or a plurality of heating chambers may be present. For example, a continuous apparatus can have a plurality of heating chambers having different treatment temperatures, and in this case the door can be omitted.

Figure 2:
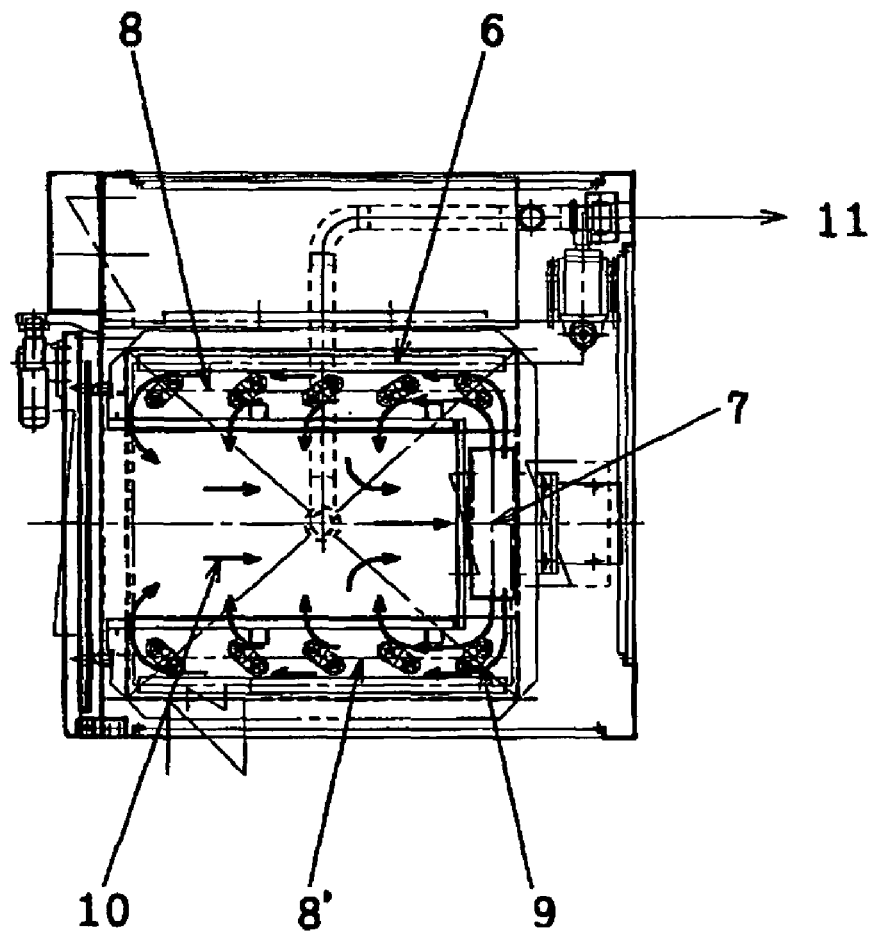
FIG. 2 is a longitudinal plan view of the apparatus of the aforementioned apparatus.

FIG. 2 is a longitudinal plan view of the aforementioned apparatus. The water heated by passage through the steam-generating heat-accumulating panel 6 is ejected as high-temperature steam into the heating chamber through a microfine steam ejection nozzle and impinges on the rotating circulation fan 7, whereby it is microfine-sized and transported into the ducts 8, 8' disposed on the left and right. It comes into contact with a heater 9 disposed within the duct 8, 8' and is heated to a prescribed temperature, and subsequently comes into contact with the material to be treated (not shown) according to the circulation flow direction 10 and heats the material to be treated. After its utilization as a heat source, the gaseous water is exhausted from the system through the exhaust outlet 11. The steam injected into the heating chamber is transported by the circulation fan 7 into the ducts 8, 8' disposed in the left side wall and right side wall of the apparatus and is heated by the heater 9.

It is important in the present invention that the temperature condition of the heater 9 suitably either match the temperature level of the injected hot water and/or steam or be set at a higher temperature. This avoids a decline in the temperature level of the injected hot water and/or steam and enables the heating chamber to be filled with gaseous water maintained at the temperature level of the injected hot water and/or steam. In contrast, such a gaseous water atmosphere cannot be formed when no heater is present. In addition, independent control of the temperature of the injected hot water and/or steam and the temperature within the heating chamber can be achieved by the independent installation and co-use of a heater for heating the interior of the heating chamber and the injected hot water and/or steam and a heating means for heating the feed water in order to generate the high-temperature steam of prescribed temperature. This avoids excessive losses in the heat content of the injected hot water and/or steam and enables an energy-saving heat treatment by the gaseous water of the material to be treated.

Figure 3:
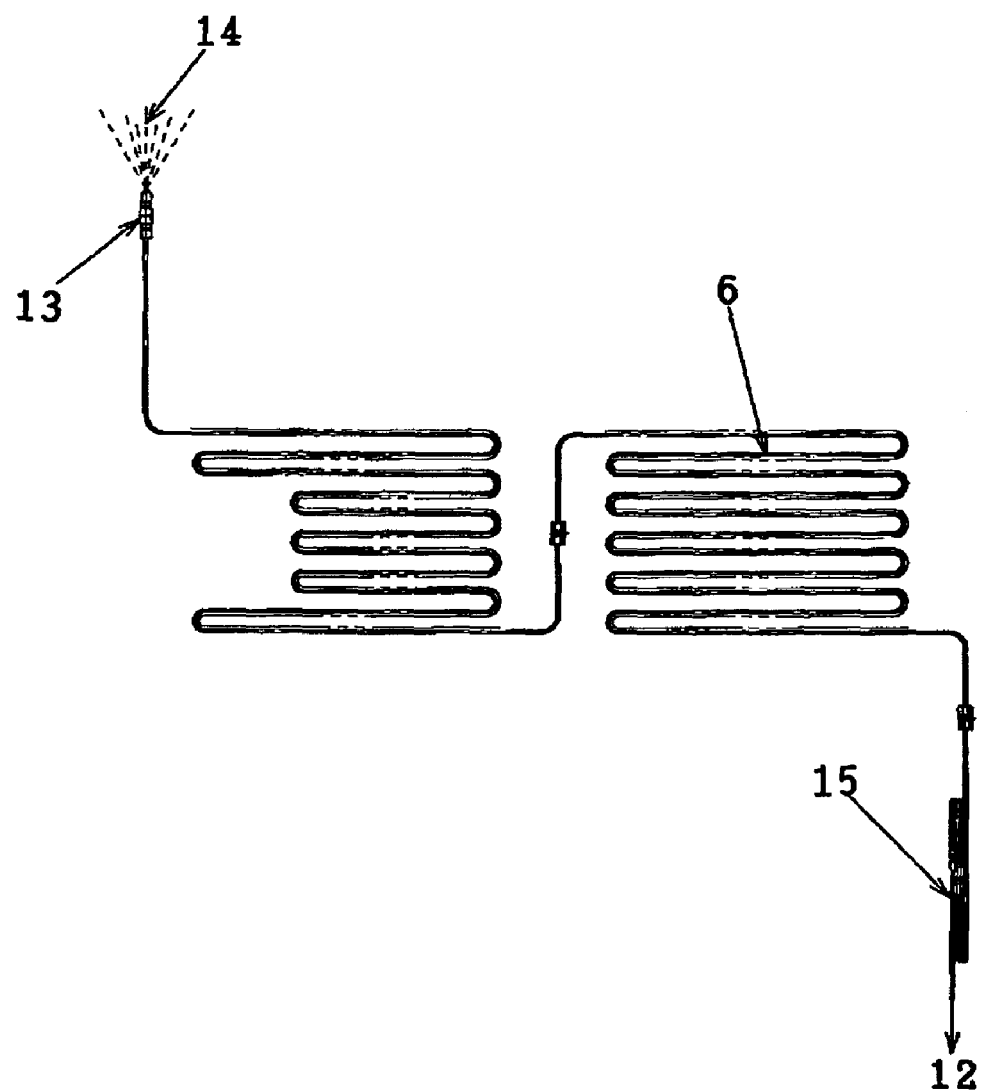
FIG. 3 is a schematic diagram of an example of a steam-generating heat-accumulating panel.

FIG. 3 shows an example of the steam-generating heat-accumulating panel of FIG. 2, wherein water fed through a feed water pump from a feed water tank is heated by passage through capillaries disposed as a heater line and microfine water particles 14 are ejected from an injection nozzle 13 disposed at the end of the capillaries. While FIG. 3 shows an example of a steam-generating heat-accumulating panel 6 comprising the combination of a plurality of U-shaped capillaries, there is no limitation to this and means having the same functionality can be similarly used. In the present invention, the water is suitably heated to 105 to 200° C. by the steam-generating heat-accumulating panel, but in order to carry out high-efficiency heating the water is preferably heated to about 108 to 115° C. and ejected. In order to utilize the gaseous water as a heating medium in the most efficient manner in the present invention, in a very suitable example hot water and/or steam heated to approximately 108 to 115° C. is ejected into a heating chamber set at approximately 108 to 115° C. However, these temperature conditions can be freely established in correspondence to the properties of the material to be treated, the type of heat treatment, the intended application of the apparatus according to the present invention, and so forth.

The gaseous water (Aqua-gas®), also referred to as AQG) is defined in the present invention as a gas component brought to a humidity of at least 90% and an oxygen concentration of no more than 1.0% and more preferably a humidity of at least 99.0% and an oxygen concentration of no more than 1.0%, by continuously injecting hot water heated to at least 100° C. by an external heater in an open system, for example, an open pipe, and/or steam into a heating chamber stably heated to at least the same temperature as the temperature of the hot water and/or steam and comprising the semi-sealed state of an open system that does not generate pressure, thereby producing water microdroplets and moist hot steam and filling the interior of the heating chamber with steam as is in an atmospheric pressure state and replacing the air. The gas component (gaseous water) produced within the heating chamber undergoes little condensation since there is no drop in temperature within the heating chamber that is being stably heated to at least the same temperature as the steam temperature. This stably maintains the high latent heat possessed by steam and the density of the ejected steam, which results in little loss of thermal energy and enables utilization as a high heat content heating medium as well as an energy-saving heating under non-oxidizing conditions. The gaseous water can preferably be maintained at a temperature, for example, of 100 to 180° C., by selecting the capacity of the external heater (panel heater) of the aforementioned open system and the capacity of the heater within the heating chamber; however, there is no limitation to this and appropriate temperature conditions can be selected in correspondence to, for example, the intended use. Gaseous water has a higher heat transfer capacity than steam or superheated steam and, for example, is very suitably used in particular for the heating and pasteurization of food products as an "Aqua-gas" heating medium that employs moist hot steam and water microdroplets, in order to enable adjustment of the initial condensation period in order to improve the processed food product yield.

Methods such as heating with ordinary steam, heating with high-temperature, high-pressure steam, and heating with a steam convection oven already exist. Among these heating methods, when, in heating with high-temperature, high-pressure steam, the high-temperature, high-pressure steam is depressurized and continuously introduced as low-pressure steam into a heating chamber implemented in a semi-sealed configuration by the disposition of an open pipe such that pressure is not generated, the heating chamber and material to be heated are heated by the thermal energy of low-pressure steam, and because of this the temperature within the heating chamber is lower than the temperature of the introduced steam. As a consequence, the steam continuously undergoes condensation and liquefaction and the amount of latent heat decreases, leading to very large energy losses. In addition, large amounts of steam and thermal energy are required in order to fill the interior of the heating chamber with low-pressure steam and maintain a residual oxygen concentration of no more than 1.0%.

When a material to be treated is heated by this heating method, a large amount of low-pressure steam is constantly transported into a heating chamber residing at a lower temperature than the introduced steam, producing condensation by heat exchange. As a consequence, for example, at 130° C. and below, the material to be treated is heated by a steaming regime due to the influence of this condensation. In the steam convection oven method of heating, on the other hand, the interior of the heating chamber is heated to a constant temperature and steam is continuously produced by the evaporation of water at the vaporization temperature; moreover, the temperature of the steam is increased by increasing the temperature of the interior of the heating chamber. The steam resides in a temperature-elevation process within the heating chamber and cannot maintain a satisfactory density or latent heat content. When a material to be treated is heated by this heating method, heating by filled steam does not occur; rather, heating occurs by steam that contains dry air, resulting in a reduced latent heat content.

In contrast to these heating methods, the heating method according to the present invention, because it generates water microdroplets and moist hot steam by continuously injecting hot water heated to at least 100° C. by an external heater in an open system, for example, an open pipe, and/or steam into a heating chamber stably heated to at least the same temperature as the temperature of the steam and residing in a semi-sealed state comprising an open tube that does not generate pressure, fills the interior of the heating chamber with steam as is in an atmospheric pressure state and replaces the air, for example, yielding a state comprising a gas component with a humidity of at least 99.0% and an oxygen concentration no greater than 1.0% and enabling the retention of a high latent heat content since the produced steam does not undergo a decline in temperature. When a material to be treated is heated by this heating method, no temperature reduction occurs within the heating chamber and there is therefore little steam condensation and a high latent heat content is maintained; in addition, a non-oxidizing heating is made possible. Moreover, the material to be treated can be subjected to continuous amplitude heating at a temperature difference of at least 10° C. in the temperature range of 90 to 180° C. In this manner the heating method according to the present invention realizes energy-saving heating at a high latent heat content, heating free from the influence of condensation, and heating under a non-oxidizing state. The characteristic features of the heating methods are compared in Table 1.

TABLE 1

|  | low-pressure steam | steam convection | gaseous water |
|---|---|---|---|
| energy-saving heating at a high latent heat content | X | X | ◯ |

TABLE 1-continued

|  | low-pressure steam | steam convection | gaseous water |
|---|---|---|---|
| heating free from the influence of condensation | X | ○ | ○ |
| non-oxidizing heating | ○ | X | ○ |

The present invention accrues the following advantageous effects, for example: 1) the present invention enables a heating and pasteurizing treatment to be carried out by subjecting the material to be treated to continuous amplitude heating at a temperature difference of at least 10° C. in the temperature range of 90 to 180° C.; 2) the present invention has the ability to substitute the interior of the heating chamber for heating the material to be treated while isolating same from the outside, with gaseous water to establish therein a gas component (gaseous water atmosphere) having a humidity of at least 99.0% and an oxygen concentration of no more than 1.0%; 3) the present invention makes it possible to rapidly heat and pasteurize a material to be treated with the aforementioned gaseous water in an efficient and minimally aggressive manner; 4) the present invention can be applied to the thawing of frozen products, to the heating, pasteurization, and cooking of agricultural products and food ingredients, and to the heating, drying, and baking of, for example, wood, metal, and ceramics; and 5) the present invention can provide a gaseous water-based heating and pasteurizing apparatus that produces gaseous water and uses same as a heating medium.

BEST MODE FOR CARRYING OUT THE INVENTION

Examples

The present invention is specifically described hereinbelow based on examples and test examples, but the present invention is in no way limited by the examples that follow.

Test Example 1

Figure 4:
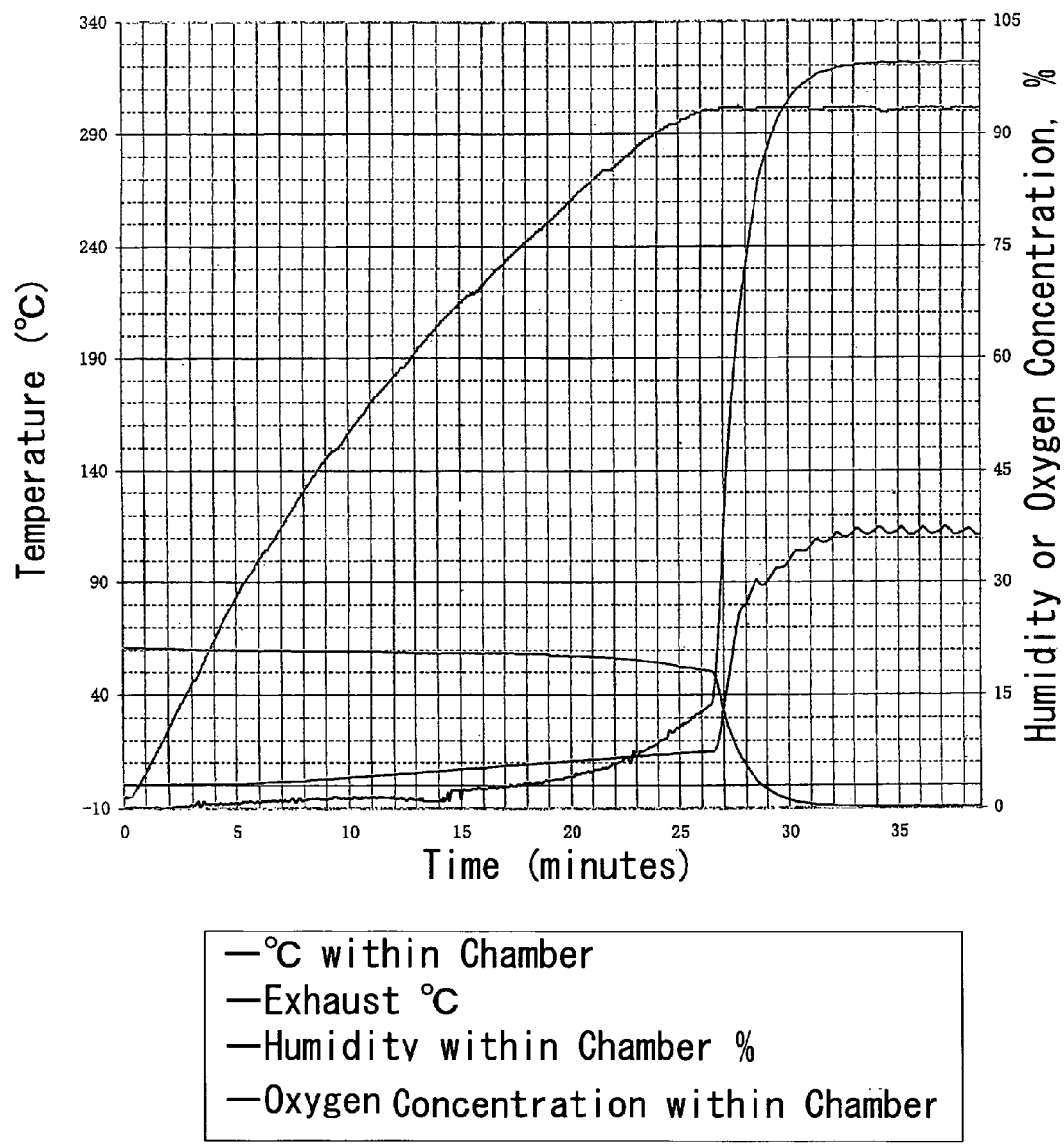
FIG. 4 shows the results of measurement of the temperature, humidity, oxygen concentration, and exhaust temperature within the chamber during the process of gaseous water production by the steam-generating apparatus.

A test of the production of Aqua-gas was carried out in this test example using the Aqua-gas-producing apparatus shown in FIG. 1. The Aqua-gas-producing apparatus was started; the semi-sealed heating chamber was heated to the same temperature as the temperature of the steam; and steam heated to 300° C. was then continuously injected into the chamber and the interior of the chamber was filled with steam as is in an atmospheric pressure state. A mixed regime of water microdroplets and moist hot steam was produced after 25 minutes had elapsed from the start of operation, and after about 7 minutes a "gaseous water" state of 99.9% humidity and a 0.01% oxygen concentration was achieved. The temperature, humidity, oxygen concentration, and exhaust temperature within the chamber were measured during the process of producing gaseous water by this Aqua-gas-producing apparatus, and the results are shown in FIG. 4. The figure demonstrates that gaseous water is produced through a sharp decline in the oxygen concentration and a sharp rise in the humidity within the chamber after 25 minutes had elapsed.

Test Example 2

Figure 5:
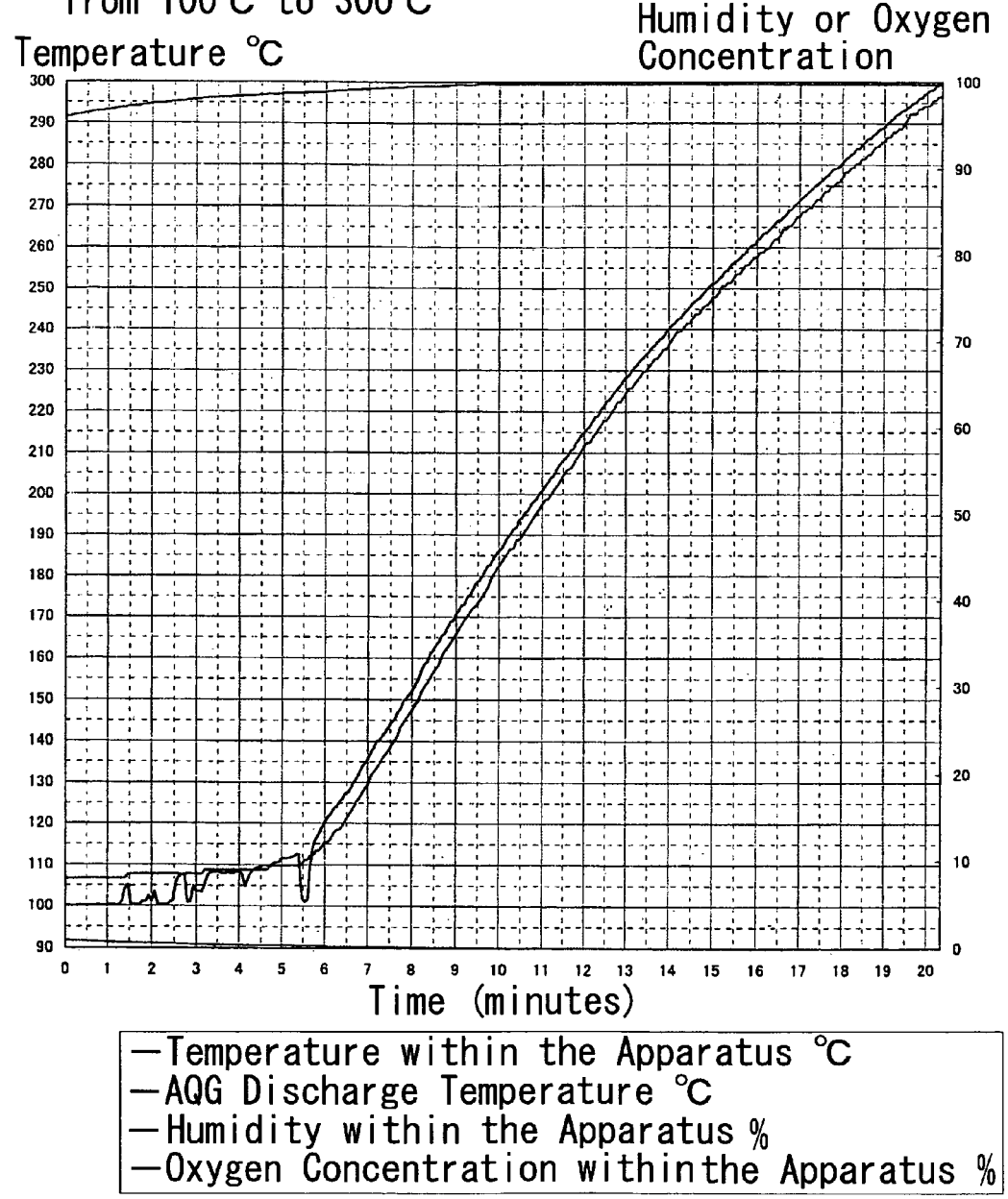
FIG. 5 shows the relationship between the temperature within the apparatus, the humidity within the apparatus, and the oxygen concentration within the apparatus and the steam discharge temperature from 100° C. to 300° C. during operation of the steam-generating apparatus using a panel heater (2 kW) for steam generation in the steam-generating apparatus and a heater (10 kW) within the heating chamber.

This test example examined the relationship between the temperature, humidity, and oxygen concentration within the apparatus and the steam discharge temperature from 100° C. to 300° C. during operation of the Aqua-gas-producing apparatus using a 2-kW steam-generating panel heater and a 10-kW heater within the heating chamber in the apparatus shown in FIG. 1. These results are shown in FIG. 5. The panel heater was set at continuous maximum operation for 100° C. and above and the heater was set at continuous maximum operation for 110° C. and above. However, at below 100° C. these were set at their set temperatures. As shown in the figure, for the steam in the vaporization and production phase of about 100 to 115° C., time is required for the temperature to increase, while the steam at above about 120° C. shows a rapid and stable temperature rise linked to the temperature within the apparatus, which demonstrated that the temperature within the apparatus and the steam temperature could be controlled in a very stable manner. On the other hand, while the steam at around 115° C. is in a quasi-stable state, it is considered to be usable as a high-density heating medium having a high latent heat content. It was thus shown that in the present invention this quasi-stable gaseous water and stable gaseous water can be utilized by freely selecting therefrom, taking advantage of their properties, in correspondence to the type of material to be heated, the purpose of the heating process, and so forth.

Test Example 3

Figure 6:
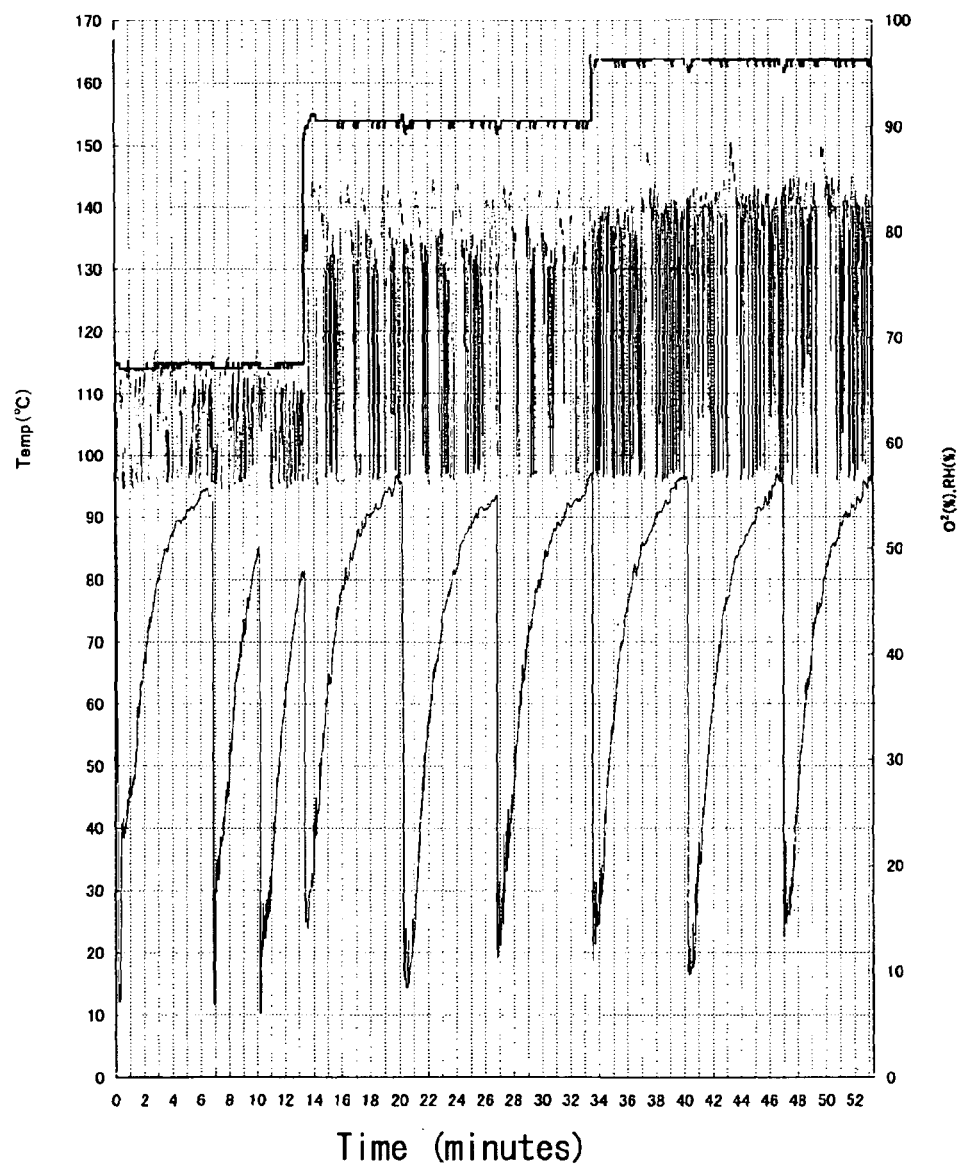
FIG. 6 shows the temperature variation in the vicinity of the steam (Aqua-gas) injection nozzle.
Figure 7:
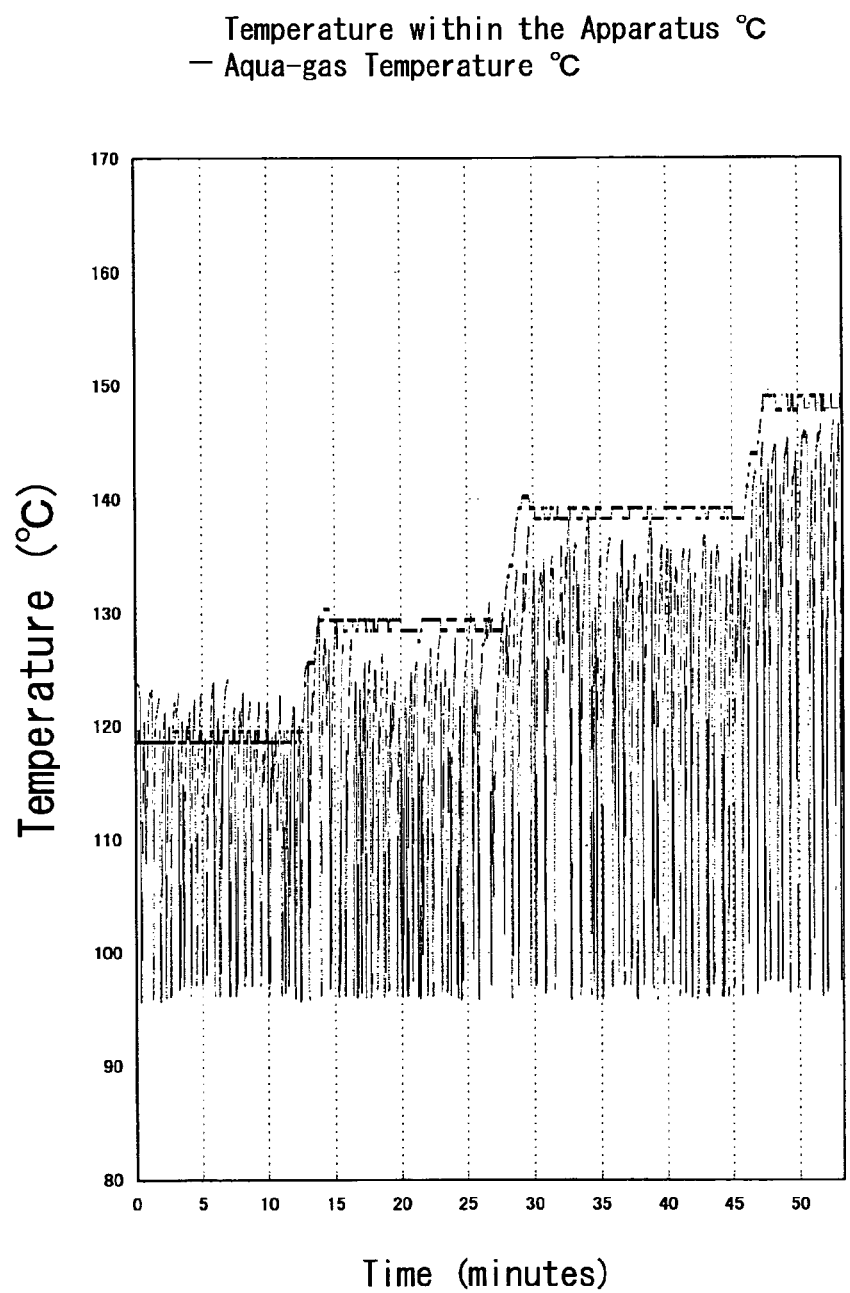
FIG. 7 shows a comparison of the temperature within the apparatus and the steam (Aqua-gas) temperature.

This test example, in use of the apparatus shown in FIG. 1, examined the temperature variation in the vicinity of the steam and water microdroplet injection nozzle during the production of gaseous water. The results are shown in FIG. 6. In accordance with the figure, it was shown that a continuous and rapid temperature variation occurred in the temperature range of about 95 to 150° C. with an amplitude for the temperature difference of about 10 to 40° C. It was also shown that the amplitude of the temperature difference and the water microdroplet and moist hot steam/dry hot steam composition can be changed by adjusting the temperature of the injected steam and the temperature within the apparatus. The temperature within the apparatus during gaseous water production was also compared with the gaseous water temperature. The feed water was preheated by the heater 15 and the feed water quantity was brought to 115 spm by a metering pump (3.62 L/h). The results are shown in FIG. 7. As shown in the figure, it was demonstrated that continuous amplitude heating at an amplitude for the temperature difference of the gaseous water of about 20 to 50° C. could be carried out by adjusting the temperature within the apparatus in the temperature range of about 120 to 150° C.

Figure 8:
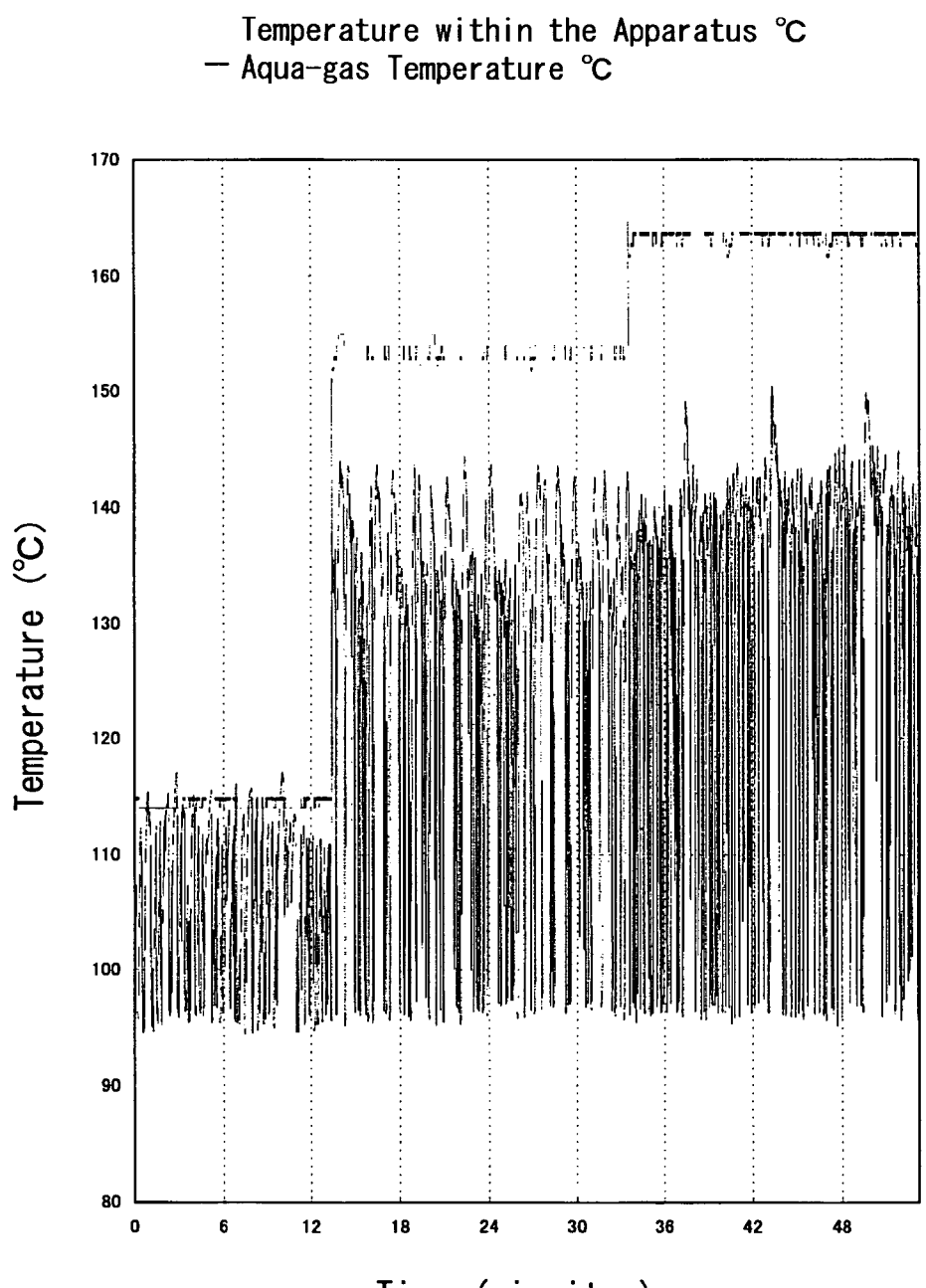
FIG. 8 shows a comparison of the temperature within the apparatus and the steam (Aqua-gas) temperature.
Figure 9:
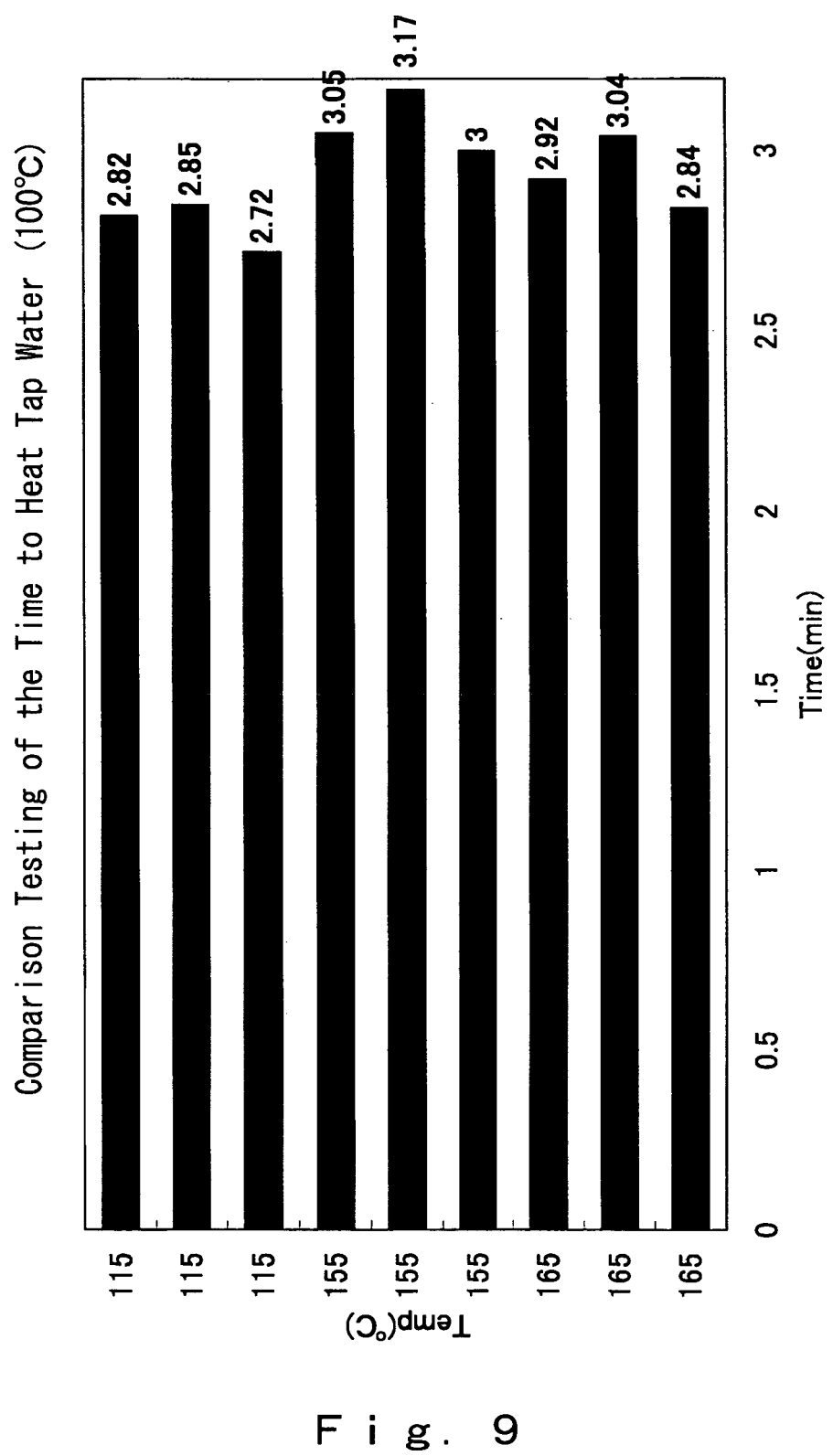
FIG. 9 shows the results of comparative testing in which tap water (100 cc) was heated to 80° C.

Proceeding as above, the temperature within the apparatus during gaseous water production was again compared with the gaseous water temperature. These results are shown in FIG. 8. As shown in the figure, it was demonstrated that continuous amplitude heating at an amplitude for the temperature difference of the gaseous water of about 20 to 50° C. could be carried out by adjusting the temperature within the apparatus in the temperature range of about 115 to 165° C. A comparison was additionally carried out of the times required to heat tap water (100 cc) to 80° C. using gaseous water in the temperature range of about 115 to 165° C. These results are shown in FIG. 9. As shown in the figure, it was demonstrated that the use of gaseous water at about 115° C. gave the shortest heating time and exhibited a high energy efficiency.

Test Example 4

Figure 10:
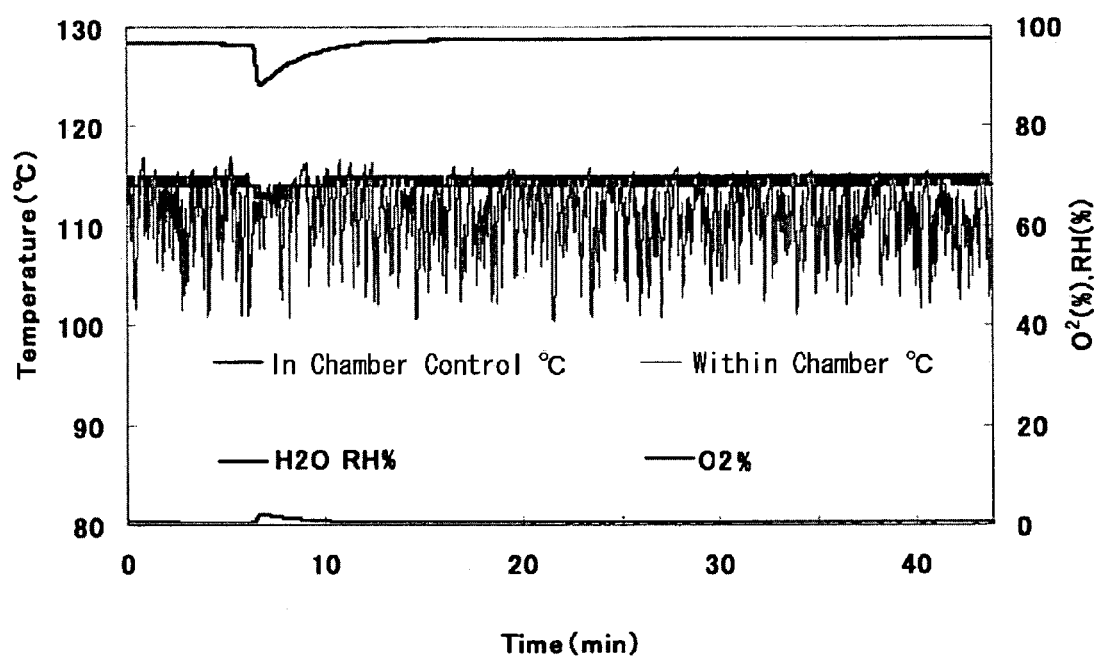
FIG. 10 shows the temperature-versus-time curve (within the chamber) for Aqua-gas at 115° C.
Figure 11:
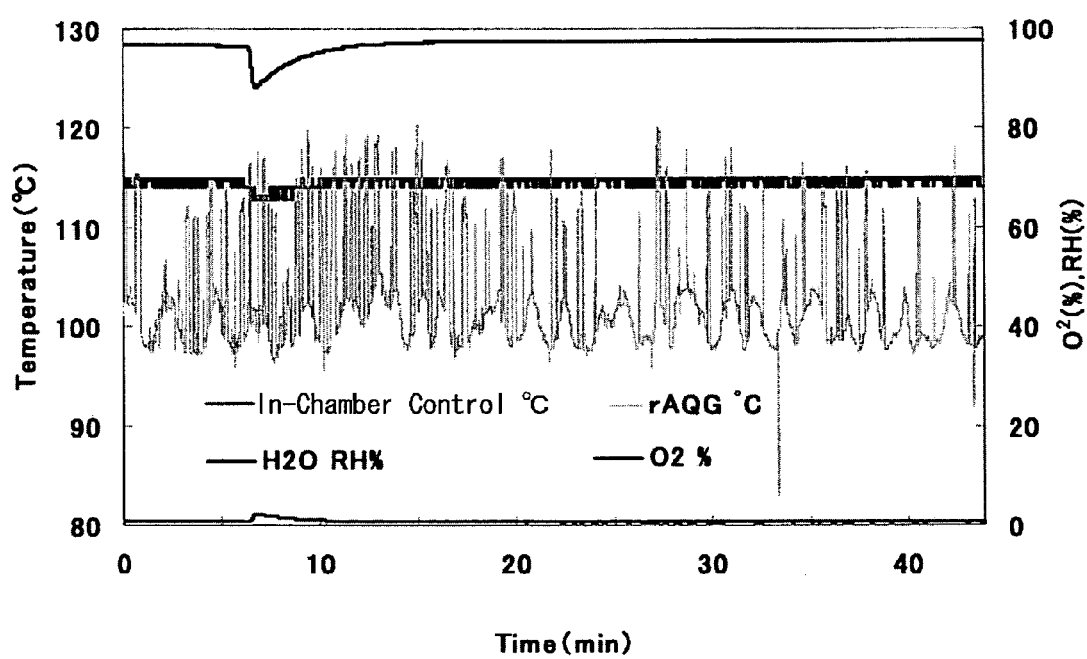
FIG. 11 shows the temperature-versus-time curve (at the injection nozzle) for Aqua-gas at 115° C.
Figure 12:
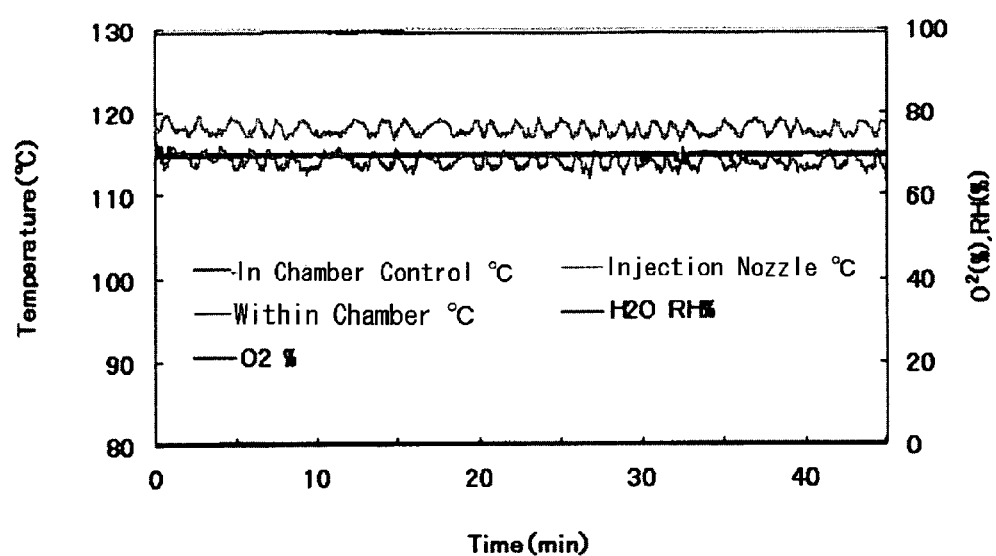
FIG. 12 shows the time course (within the chamber and at the injection nozzle) of the temperature for the condition of superheated steam at 115° C.
Figure 13:
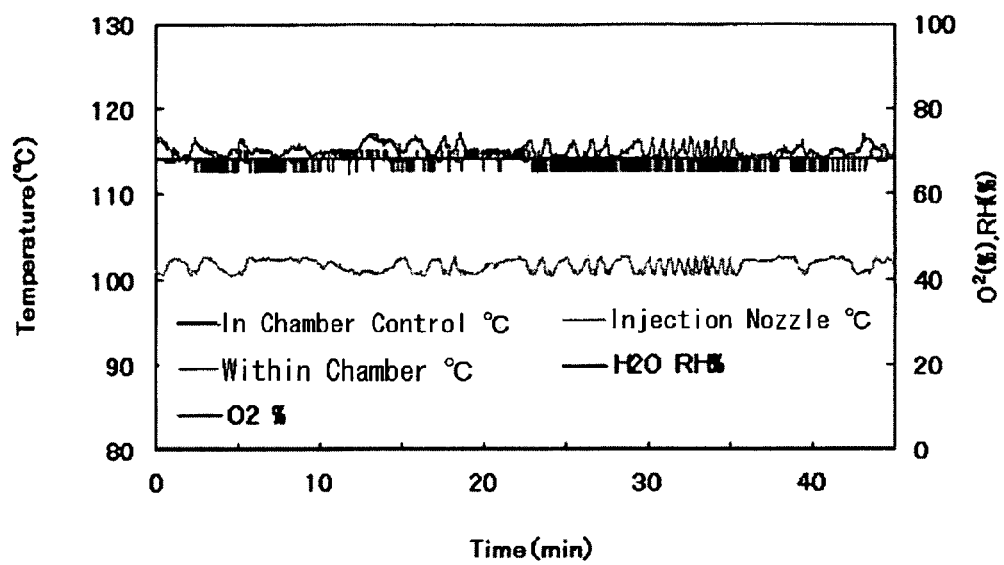
FIG. 13 shows the time course (within the chamber and at the injection nozzle) of the temperature for the condition of saturated steam at 115° C.
Figure 14:
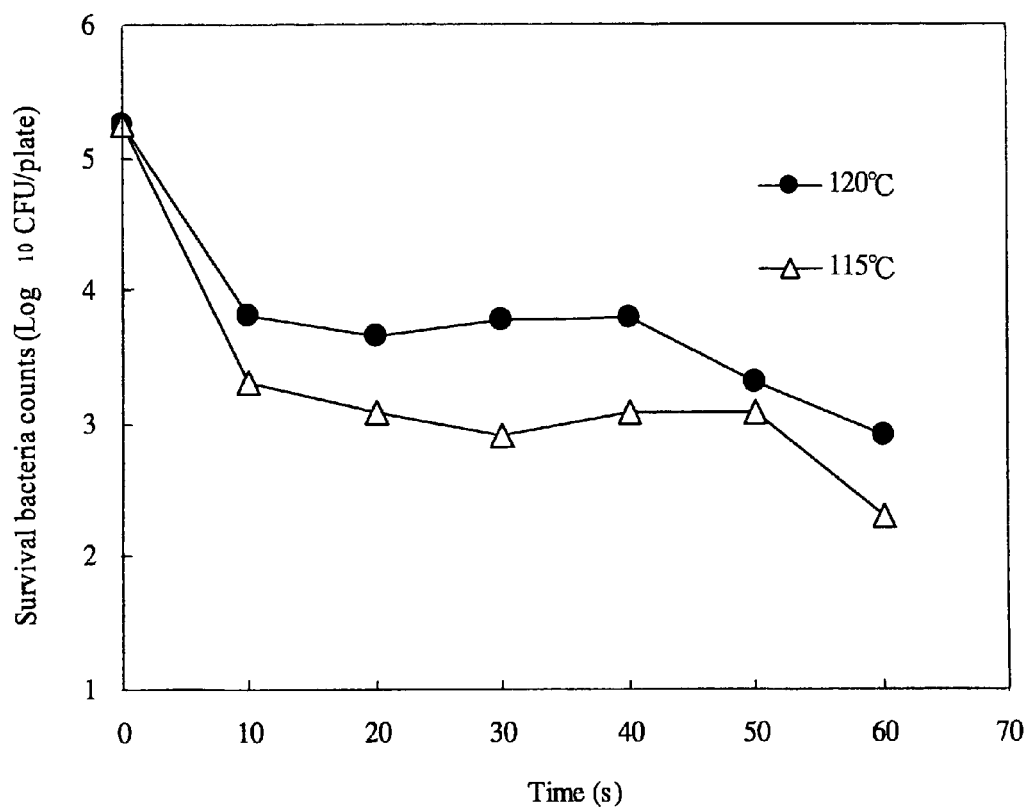
FIG. 14 shows the change due to Aqua-gas in the *Bacillus subtilis* spore count on horizontal agar plates.

Proceeding as in Test Example 3, the relationship between time and the temperature of the elaborated Aqua-gas was examined. FIG. 10 shows the temperature-versus-time curve within the chamber for 115° C. Aqua-gas, while FIG. 11 shows the temperature-versus-time curve at the injection nozzle for 115° C. Aqua-gas. For comparison, temperature-versus-time curves (within the chamber and at the injection nozzle) for superheated steam and saturated steam are shown in FIGS. 12 and 13. It is demonstrated that the temperature-versus-time curves for Aqua-gas are essentially different from the temperature-versus-time curves for superheated steam and saturated steam.

Example 1

Various foods were subjected to a heating and pasteurizing treatment with Aqua-gas in this example.

1) Effect on the Overall Viable Bacteria Count

Various foods were submitted to treatment with Aqua-gas under the following conditions.

Cucumber 3 minutes, spinach 10 seconds, strawberry 10 seconds, potato 16 minutes (round, achieved center temperature=75° C.), soybean (24 hour immersion in alkaline ionized water) 20 minutes, kidney bean (24 hour immersion in alkaline ionized water) 20 minutes, black soy bean (24 hour immersion in alkaline ionized water) 20 minutes, rice (40 minute immersion in alkaline ionized water followed by thermal cooking with Aqua-gas for 25 minutes). The results are shown in Table 2. It may be understood from the table that Aqua-gas treatment exhibits a significant pasteurizing effect on vegetables (excluding spinach) and grains.

TABLE 2 overall viable bacteria count

| | pretreatment | | after immersion measured | | post-treatment | |
|---|---|---|---|---|---|---|
| | measured CFU/g | Log CFU/g | sured CFU/g | Log CFU/g | measured CFU/g | Log CFU/g |
| cucumber | 180000 | 5.26 | | | 50 | 1.70 |
| spinach | 26000 | 4.41 | | | 6100 | 3.79 |
| strawberry | 180 | 2.26 | | | 0 | 0.00 |
| potato | 18600 | 4.27 | | | 80 | 1.90 |
| soybean | 160 | 2.20 | 100 | 2.00 | 0 | 0.00 |
| kidney bean | 0 | 0.00 | 0 | 0.00 | 0 | 0.00 |
| black soybean | 4500 | 3.65 | 54000 | 4.73 | 0 | 0.00 |
| rice | 6000 | 3.78 | 1000 | 3.00 | 430 | 2.63 |

2) Effects on the *E. coli* Group

The pasteurizing effect on the *E. coli* group was examined by treating various foods with Aqua-gas under the conditions shown in Table 3. The results are shown in Table 3. It may be understood from the table that Aqua-gas treatment has a much stronger pasteurizing effect than the heretofore used heating.

TABLE 3

| | preserving conditions | | |
|---|---|---|---|
| test section (treatment time) | initial *E. coli* group count/g | after 24 hours at 25° C. *E. coli* group count/g | after 48 hours at 25° C. *E. coli* group count/g |
| potato (42 minutes) | negative | negative | negative |
| control: steaming (60 minutes) | negative | negative | negative |
| cucumber (30 seconds) | negative | negative | negative |
| control: boiling (30 seconds) | negative | negative | $9.4 \times 10^4$ |
| onion (30 seconds) | negative | negative | negative |
| control: boiling (30 seconds) | negative | $3.0 \times 10^3$ | $6.0 \times 10^5$ |
| lettuce (20 seconds) | negative | negative | $4.0 \times 10^2$ |
| control: boiling (20 seconds) | negative | $5.3 \times 10^2$ | $5.0 \times 10^4$ |
| cabbage (30 seconds) | negative | negative | negative |
| control: boiling (30 seconds) | negative | $5.0 \times 10$ | $3.0 \times 10^4$ |

3) Effects Against Fungi/Yeast

The pasteurizing effect against fungi/yeast was examined by subjecting various foods to treatment with Aqua-gas as in Example 1. The results are shown in Table 4. It may be understood from the table that the fungus count on Aqua-gas-treated vegetables and grains was substantially reduced.

TABLE 4 fungu/yeast count

| | pretreatment | | after immersion measured | | post-treatment | |
|---|---|---|---|---|---|---|
| | measured CFU/g | Log CFU/g | sured CFU/g | Log CFU/g | measured CFU/g | Log CFU/g |
| cucumber | 2800 | 3.45 | | | 0 | 0.00 |
| spinach | 900 | 2.95 | | | 30 | 1.48 |
| strawberry | 830 | 2.92 | | | 0 | 0.00 |
| potato | 160 | 2.20 | | | 0 | 0.00 |
| soybean | 0 | 0.00 | 0 | 0.00 | 0 | 0.00 |
| kidney bean | 0 | 0.00 | 0 | 0.00 | 0 | 0.00 |
| black soybean | 0 | 0.00 | 0 | 0.00 | 0 | 0.00 |
| rice | 140 | 2.15 | 0 | 0.00 | 0 | 0.00 |

4) Effects Against Heat-Resistant Spore-Formed Bacteria

The pasteurizing effect for heat-resistant spore-formed bacteria was examined by subjecting *Bacillus subtilis*, vegetables, and grains to treatment with Aqua-gas. The results are shown in Table 5. From the table it may be understood that $10^5$ CFU/mL *Bacillus subtilis* spores coated on a standard agar medium were rapidly pasteurized by a brief 60 seconds of Aqua-gas and that Aqua-gas-treated grains and potato were substantially pasteurized.

TABLE 5

| | heat-resistant bacteria count | | | | | |
|---|---|---|---|---|---|---|
| | pretreatment | | after immersion | | post-treatment | |
| | measured CFU/g | Log CFU/g | measured CFU/g | Log CFU/g | measured CFU/g | Log CFU/g |
| potato | 5600 | 3.75 | | | 20 | 1.30 |
| soybean | 20 | 1.30 | 0 | 0.00 | 0 | 0.00 |
| kidney bean | 0 | 0.00 | 0 | 0.00 | 0 | 0.00 |
| black soybean | 150 | 2.18 | 30 | 0.00 | 0 | 0.00 |
| rice | 30 | 1.48 | 0 | 0.00 | 0 | 0.00 |

Example 2

The Aqua-gas heating and pasteurizing treatment of various foods and the storage stability of pasteurized foods were examined in this example.

1) Vegetables
(1) Pretreatment
spring daikon: after peeling, cut to 3 cm-thick disks
fresh onion: peeled and sliced to 3 mm
fresh bamboo shoot: peeled and sliced to 5 mm
fresh cucumber: 3 mm slices
spring cabbage: cored and randomly chopped
fresh broccoli: the stems were cut off
carrot: peeled and cut in 3-mm quarters
fresh corn: shucked leaving one layer, with cob danshakuimo (Irish Cobbler): as obtained after washing with running tap water
skinless cut danshakuimo: the peeled potato was cut into bite-sized pieces and then washed with running tap water
(2) Test of Aqua-Gas Heating and Pasteurization The prepped vegetables were placed on a prescribed tray and a temperature sensor was inserted into the center of one specimen and was set so as to enable measurement of the core temperature. After the completion of heating, the specimen was placed in a sterile bag and was gradually cooled with cold running water. "Boiled" and "steamed" were the control treatments. The results are reported in Table 6.

TABLE 6

| | AQG pasteurization conditions | | yield | general viable microorganism count | | sensorial evaluation |
|---|---|---|---|---|---|---|
| sample | minutes | °C. | (%) | initial | storage time (conditions) | |
| spring daikon | 22 | approx. 95 | 97 | 0 | <300 (after cold storage for 10 days) | relative to the control, the panel testing results and the food-making properties were good |
| spring daikon (control) | 40 | boiled | 95 | <300 | 4 × 10² (after cold storage for 10 days) | |
| fresh onion | 1 | 75 | 101 | <300 | <300 (24 hours at 25° C.) | relative to the control, the panel testing results and the food-making properties were good |
| fresh onion (control) | 1 | boiled | 95 | <300 | 10⁴ (24 hours at 25° C.) | |
| fresh carrot | 1.5 | — | 97 | <300 | <300 (4 days at 10° C.) | relative to the control, both the texture and taste were good |
| fresh carrot (control) | 3 | boiled | 94 | <300 | 3.0 × 10² (4 days at 10° C.) | |
| fresh bamboo shoot | 5 | 75 | 100 | 0 | <300 (after cold storage for 10 days) | relative to the control, the panel testing results and the food-making properties were good |
| boiled plain (control) | | retort | | | | |
| spring cabbage | 1 | — | 102 | <300 | <300 (4 days at 10° C.) | relative to the control, both the texture and taste were good |
| spring cabbage (control) | 1 | boiled | 96 | <300 | 5.0 × 10² (4 days at 10° C.) | |
| fresh corn | 7 | approx. 85 | 105 | 0 | <300 (after cold storage for 90 days) | relative to the control, the panel testing results were good |
| fresh corn (control) | 7 | boiled | 95 | 0 | <300 (after cold storage for 90 days) | |
| fresh edamame | 2.7 | approx. 94 | 93 | 0 | <300 (after cold storage for 90 days) | relative to the control, the panel testing results were good |
| fresh edamame (control) | 6 | boiled | 90 | 0 | <300 (after cold storage for 90 days) | |
| fresh broccoli | 2.8 | approx. 94 | 99 | 0 | <300 (after cold storage for 30 days) | no fading after cold storage for 30 days |
| fresh broccoli (control) | 7 | boiled | 135 | 0 | 4.0 × 10³ (after 4 days at 10° C.) | substantial water absorption and fading |

TABLE 6-continued

| sample | AQG pasteurization conditions minutes | AQG pasteurization conditions °C. | yield (%) | general viable microorganism count initial | general viable microorganism count storage time (conditions) | sensorial evaluation |
|---|---|---|---|---|---|---|
| danshakuimo (peeled) | 35 15 | approx. 95 approx. 95 | 97 | 0 | <300 (after cold storage for 7 days) | the texture and palatability were both very good |
| danshakuimo (peeled and halved) | 14 | approx. 98 | 100 | 0 | <300 (after 5 days at 10° C.) | relative to the control, the texture and taste were good after 5 days |
| danshakuimo (peeled and halved) (control) | 20 | steamed | 100 | <300 | <300 (after 5 days at 10° C.) | |
| danshakuimo (round) | 25 | approx. 95 | 97 | 0 | <300 (after cold storage for 10 days) | compared to the control, the texture and palatability were both good |
| danshakuimo (round) (control) | 40 | steamed | 95 | 0 | | |
| danshakuimo (peeled, randomly cut) | 3 | approx. 75 | 102 | 0 | <300 (after cold storage for 7 months) | after French-frying, the texture and palatability were both good |
| danshakuimo (with skin, cut into 8 pieces) | 3.4 | approx. 75 | 102 | 0 | <300 (after cold storage for 10 days) | after French-frying, the texture and palatability were both very good |

Example 3

The keeping qualities of side dishes were examined in this example using Aqua-gas-pasteurized vegetables.
1) Vegetable-Loaded Potato Salad
AQG danshakuimo: 46.4% (the material prepared in Example 2 was used after mashing)
AQG carrot: 10% (the material prepared in Example 2 was used)
AQG cabbage: 10% (the material prepared in Example 2 was used)
AQG cucumber: 10% (the material prepared in Example 2 was used)
AQG onion: 7.1% (the material prepared in Example 2 was used)
mayonnaise: 15%
johakuto white sugar: 1%
fresh cream: 0.4%
salt: 0.1%
pepper: 0.01%

The overall viable bacteria count for the "vegetable-loaded potato salad" prepared using this recipe was initially 300 or less and was 300 or less even after keeping for 4 days at 10° C. The overall viable bacteria count for a "vegetable-loaded potato salad" prepared from ingredients subjected to the usual heat treatment was initially $15 \times 10^3$ and after keeping for 4 days at 10° C. had reached $90 \times 10^5$.

2) Simmered Kabocha Squash
freezed cut kabocha squash: 1 kg
liquid seasoning (spray): 10 g (14.2% soy sauce, 14.2% mixed soup stock, 71.6% water)
johakuto white sugar (coat): 80 g "Simmered kabocha squash" prepared by heating this recipe for 11 minutes with Aqua-gas had an overall viable bacteria count of 300 or less both initially and after keeping for 4 days at 10° C. The control, which was cooked by steaming for 11 minutes, had an initial overall viable bacteria count of 300 or less, but had a count after 4 days at 10° C. of $11 \times 10^4$.

3) Simmered Daikon
AQG daikon: 48% (the material prepared in Example 2 was used after halving)
soy sauce: 3.94%
johakuto white sugar: 5.91%
seasoning base: 1.75% (granular)
chicken soup stock: 0.88% (granular)
water: 39.6%

"Simmered daikon" prepared by the usual method using this recipe had an overall viable bacteria count of 300 or less both initially and after keeping for 4 days at 10° C. On the other hand, the control product, which was cooked with daikon boiled for 40 minutes in water, had an initial overall viable bacteria count of 300 or less, but had a count after 4 days at 10° C. of $56 \times 10^3$.

4) Tosa-Style Simmered Fresh Bamboo Shoots
AQG fresh bamboo shoots: 49.5% (the material prepared in Example 2 was used after quartering)
soy sauce: 4.94%
mirin: 4%
johakuto white sugar: 3.2%
seasoning base: 0.82% (granular)
chicken soup stock: 0.16% (granular)
seasoning of full body: 0.16%
dried bonito flakes: 0.2%
water: 37%

The "Tosa-style simmered fresh bamboo shoots" prepared by the usual method using this recipe had an overall viable bacteria count of 300 or less both initially and after keeping for 4 days at 10° C. "Tosa-style simmered fresh bamboo shoots" prepared from commercially available "boiled bamboo shoots" similarly had an overall viable bacteria count of 300 or less both initially and after keeping for 4 days at 10° C.; however, the flavor, texture, and aroma of the AQG recipe were far better.

Example 4

In this example, raw milk was heated with Aqua-gas and a test was carried out of minimally aggressive pasteurization by heating raw milk with Aqua-gas.

Fresh raw milk (the same day as milking) that was a precursor for a commercial product (Special Undiluted Milk from Yamakawa Farm (628, Aza Onuma-cho, Nanae-cho, Kameda-gun, Hokkaido)) was specially procured from Yamakawa Farm and was subjected to the preprocessing described below followed by heating in a gaseous water pasteurizing apparatus under the specified conditions and a prescribed post-treatment. This was followed by the specified examination of the overall viable bacteria count.

(1) The Preprocessing Procedure

Several hundred grams (liquid depth of 30 to 35 mm) of the raw milk was taken to a stainless steel bowl in a clean bench and a temperature sensor was fixed in the center of the liquid.

(2) Test of Pasteurization by Heating with Aqua-Gas

The bowl was set in an Aqua-gas pasteurizing apparatus and heating to the specified temperature was carried out. This was followed by gradual cooled in the clean bench and submission to the examination of the overall viable bacteria count.

(3) Results of the Examination of the Initial Overall Viable Bacteria Count

The results of measurement by a standard horizontal agar plate cultivation method are shown in Tables 7 and 8. An effective pasteurization effect was shown both for central temperature=95° C./1 minute holding and for an achieved central temperature of 85° C. The results of a primary sensorial evaluation were also good and there was no change in appearance with a favorable critique to the effect that the characteristic "milk odor" was absent and the product was smooth and easy to drink.

(4) Preserving Tests

Tests were carried out on the keeping characteristics in cold storage (3 to 5° C.) and on holding at room temperature (average=25° C.). The overall viable bacteria count was measured at specified time intervals. These results are shown in Tables 7 and 8. Yamakawa Farm's Special Undiluted Milk (nonhomogenized additive-free unmodified product pasteurized for 15 minutes at 75° C.; expiration: within five days stored at 10° C. or below) was used for the control. For the cold storage keeping conditions, the viable bacteria count was zero after both 3 weeks and 1 month for both 95° C./1 minute and 85° C. For the room temperature keeping conditions, the viable bacteria count was zero after 7 days for 95° C./1 minute, while separation had begun after 12 days. On the other hand, the viable bacteria count for the 85° C. product had reached to more than $10^6$ when 5 days had elapsed. For the commercial product, the viable bacteria count was zero after 5 days and had reached to more than $10^6$ on the 7th day. The results of these batch-type experiments are suggestive of an efficacy in continuous methods (capillary methods and thin-film methods).

TABLE 7

| sample designation | Aqua-gas pasteurization conditions | | results of measurement of the overall viable bacteria count | | | results of the sensorial evaluation |
|---|---|---|---|---|---|---|
| | minutes | central temperature (° C.) | initial | 3 weeks | 1 month | |
| raw milk | 3 | approx. 85 | 0 | 0 | 0 | even after 1 month in cold storage, the milk odor was absent and the product was smooth and easy to drink |
| raw milk | 1 | 95 | 0 | 0 | — | after 3 weeks in cold storage, the milk odor was absent and the product was smooth and easy to drink |
| commercial milk* | (15) | (75) | 0 | 0 (1 week) | — | |

*heated for 15 minutes at 75° C.

TABLE 8

| sample designation | Aqua-gas pasteurization conditions | | results of measurement of the overall viable bacteria count | | | results of the sensorial evaluation |
|---|---|---|---|---|---|---|
| | minutes | central temperature (° C.) | initial | after 5 days | after 7 days | |
| AQG raw milk | 3 | approx. 85 | 0 | >$10^6$ | — | |
| AQG raw milk | 1 | 95 | 0 | — | 0 | even after 7 days at room temperature, the milk odor was absent and the product was smooth and easy to drink |
| commercial milk* | (15) | (75) | 0 | 0 | >$10^6$ | |

*heated for 15 minutes at 75° C.

Example 5

Rice and grain were submitted to an Aqua-gas heating and pasteurization treatment in this example.

(Pasteurization Test on Rice)

A commercially available rice (Koshihikari) was directly submitted to Aqua-gas pasteurization. The results of measurement of the initial bacteria count by a conventional method are shown in Table 9.

TABLE 9

|  | unheated | heated for 30 seconds | heated for 60 seconds | heated for 180 seconds |
| --- | --- | --- | --- | --- |
| overall viable bacteria count | 0 | 0 | 0 | 0 |

(Evaluation of the Keeping Qualities and Taste for Rice-Cooking with Aqua-Gas)

A commercially available rice (Koshihikari) was washed with tap water, taken up in a bamboo basket and drained, and then transferred to a stainless steel bowl. 1.2-fold (volume) water was added and the rice was immersed for 90 minutes while being held in a refrigerator, after which it was cooked for 35 minutes by heating with Aqua-gas. After steaming for 15 minutes and cooling, the rice was submitted to a primary sensorial evaluation and measurement of the initial bacteria count. The rice was also placed in a lidded transparent plastic container in order to carry out a test of the keeping quality. In addition, the commercially available rice (Koshihikari) was washed with tap water, taken up in a bamboo basket and drained, then transferred to a stainless steel bowl, combined with 1.1-fold (volume) water, immersed for 40 minutes while being held in a refrigerator, and then cooked for 30 minutes by heating with Aqua-gas. After steaming for 10 minutes and cooling, this rice was submitted to the primary sensorial evaluation and measurement of the initial bacteria count and was also placed in a lidded transparent plastic container in order to carry out a test of the keeping quality. These results are reported in Table 10.

TABLE 10

|  | initial | 48 hr | 72 hr | 96 hr | sensory test |
| --- | --- | --- | --- | --- | --- |
| AQG-cooked-i) | 0 | 0 | 0 | 0 | Cooking resulted in a good aroma and delicious flavor; however, the moisture content was excessive. This same evaluation also applied after 48 hours. The taste dropped off somewhat after 72 hours. At 96 hours, the taste was in decline; the texture was unchanged. |
| AQG-cooked-ii) | 0 | 0 | 0 | 0 | Cooking resulted in a good aroma and delicious flavor; however, the moisture content was somewhat high. This same evaluation also applied after 48 and 72 hours. After 96 hours, the taste was trending downward; the texture was unchanged. |

(Rice and Red Beans)

Red azuki beans were washed with water and then immersed in 3-fold water and heated with Aqua-gas for 10 minutes; the cooking liquid was drained off and the beans were heated for another 10 minutes with Aqua-gas in 3-fold water. Mochigome rice was then washed and immersed for 1 hour in the cooking liquid from the red azuki beans and was thereafter drained. After heating this for 20 minutes with Aqua-gas, 2.4% salt water was sprinkled on and, after 5 seconds, heating with Aqua-gas was carried out again for 10 minutes. The resulting AQG rice and red beans had an overall viable bacteria count no greater than 300 both initially and also after keeping for 48 hours at 25° C. In contrast, rice and red beans steamed in a bamboo steamer by the usual method had an overall viable bacteria count initially of no more than 300, but had a viable bacteria count of $50 \times 10^5$ after keeping for 48 hours at 25° C.

Example 6

Several legumes were submitted to heating and pasteurization with Aqua-gas in this example.

Taishokintoki beans (red kidney beans) and azuki beans were immersed in 4-fold alkaline ionized water for 38 hours in a refrigerator, drained, and spread out on a tray and subjected to Aqua-gas heating and pasteurization.

The Taishokintoki beans were heated for 40 minutes, while the azuki beans were heated for 20 minutes. After heat radiation, the beans were submitted to primary sensorial evaluation and measurement of the initial bacteria count. These results are reported in Table 11.

TABLE 11

|  | initial | 48 hours | sensory test |
| --- | --- | --- | --- |
| kidney beans-(1) | 0 | — | Good aroma and delicious flavor, but hard when cooled. Beans cooked by the usual method had a delicious flavor, but were somewhat hard. Stable even after standing for 2 months at room temperature in a vacuum pack. |
| kidney beans-(2) | 0 | $1.2 \times 10^3$ | The aroma and flavor were weaker than in (1); however, the beans were |

TABLE 11-continued

| | initial | 48 hours | sensory test |
|---|---|---|---|
| | | | tender even when cooled and there was no astringent taste. Stable even after standing at room temperature for 48 hours; decomposition began after 72 hours. |
| azuki beans-(1) | 0 | — | Immediately after, good aroma and delicious flavor, but some astringency remained. Stable even after standing for 2 months at room temperature in a vacuum pack. |
| azuki beans-(2) | 0 | $3 \times 10^3$ | Immediately after, good aroma and delicious flavor; astringency was also absent. Stable even after standing at room temperature for 48 hours, but a decomposition trend appears after 72 hours. |

Example 7

Seafood was subjected to Aqua-gas heating and pasteurization in this example.
(Storage Characteristics and Taste of Sea Urchin)

A commercially available raft product was laid out on aluminum foil one at a time and a temperature sensor was set in the center of the sea urchin; this was followed by Aqua-gas heating and pasteurization. After heat radiation, the yield and initial bacteria count were measured, sensorial evaluation was carried out, and a cold storage test was run by vacuum packaging with an oxygen scavenger enclosed. These results are shown in Table 12.

TABLE 12

| | | overall viable bacteria count | | |
|---|---|---|---|---|
| yield (%) | initial | cold storage (6 months) | sensorial evaluation | |
| 105 | <300 | <300 | Had the taste of steamed sea urchin and a delicious flavor; good shape retention and color; color was maintained even after keeping for 6 months. | |

(Storage Characteristics and Flavor of Fish Roe (Walleye Pollock))

Commercially available raw fish roe (walleye pollock) was laid out on a wire mesh and submitted to a test of Aqua-gas heating and pasteurization. After heat radiation, the yield and initial bacteria count were measured, sensorial evaluation was carried out, and a cold storage test was run by vacuum packaging with an oxygen scavenger enclosed. These results are shown in Table 13.

TABLE 13

| | | overall viable bacteria count | |
|---|---|---|---|
| yield (%) | initial | cold storage (3 months) | sensorial evaluation |
| 105 | <300 | <300 | Vivid pink with excellent texture and flavor; shape retention is good. These same qualities were retained even after keeping for 3 months. |

(Cooking Characteristics, Flavor, and Storage Characteristics of Salt-Preserved Cod Roe)

A commercially available cold- and salt-preserved cod roe was laid out without modification on a wire mesh and submitted to a test of Aqua-gas heating and pasteurization. After heat radiation, the yield and initial bacteria count were measured, sensorial evaluation was carried out, and a cold storage test was run by vacuum packaging with an oxygen scavenger enclosed. These results are shown in Table 14.

TABLE 14

| | | overall viable bacteria count | |
|---|---|---|---|
| yield (%) | initial | cold storage (3 months) | sensorial evaluation |
| 101 | <300 | <300 | Excellent texture with good flavor and good shape retention. These same qualities were retained even after keeping sealed in cold storage for 3 months. |

Example 8

The improvement in the long-term storage stability (extended effects) of Aqua-gas heated and pasteurized foods was examined in this example. The results are shown below.

1) Seafood

Aqua-gas pasteurized "raw sea urchin" had an overall bacteria count no greater than 300 after cold storage for 6 months sealed in a package with an oxygen scavenger. Aqua-gas heated and pasteurized "shucked scallops" had an overall bacteria count no greater than 300 after cold storage for 7 months sealed in a package with an oxygen scavenger. Even after cold storage for 3 months sealed in a package with an oxygen scavenger, Aqua-gas heated and pasteurized "shucked oysters" presented no discoloration and no appearance of dripping and had also retained their shape. In addition, after cold storage for 3 months sealed in a package with an oxygen scavenger, Aqua-gas heated and pasteurized "raw cod roe" had good color, was free of dripping, and was in a good condition of storage.

2) Agricultural Products

After cold storage for 6 months in a sealed package while exposed to a fluorescent lamp, Aqua gas heated "peeled and cut danshakuimo" was free of discoloration and dripping, had a residual vitamin C content of 85%, and presented good shape retention. The overall viable bacteria count was also 300 or less. It could be cooked into a fried potato test food. Aqua-gas heated "round danshakuimo" could be cold-stored for 12 months in a sealed package. It could be cooked into a fried potato test food. The residual vitamin C content was 35% and the overall viable bacteria count was 300 or less. Aqua-gas heated and pasteurized "corn (on cob)" had an overall bacteria count of 300 or less after cold storage for 6 months sealed in a package with an oxygen scavenger.

Example 9

The presence of the Aqua-gas water microdroplets was examined in this example using a high-speed camera. The nozzle used had an orifice diameter of 1.9 mm; the water quantity was 50 mL/minute; the temperature was 115° C.; and general Aqua-gas treatment conditions were used. The water microdroplets were photographed using a high-speed camera (Photron, FASTCAM-APX RS 250 K). The frame rate was 5000 fps and the exposure time was $\frac{1}{258000}$ second. The region photographed ranged from the vicinity of the nozzle ejection orifice to 80 mm therefrom, and also the position at 220 mm therefrom.

Figure 15:
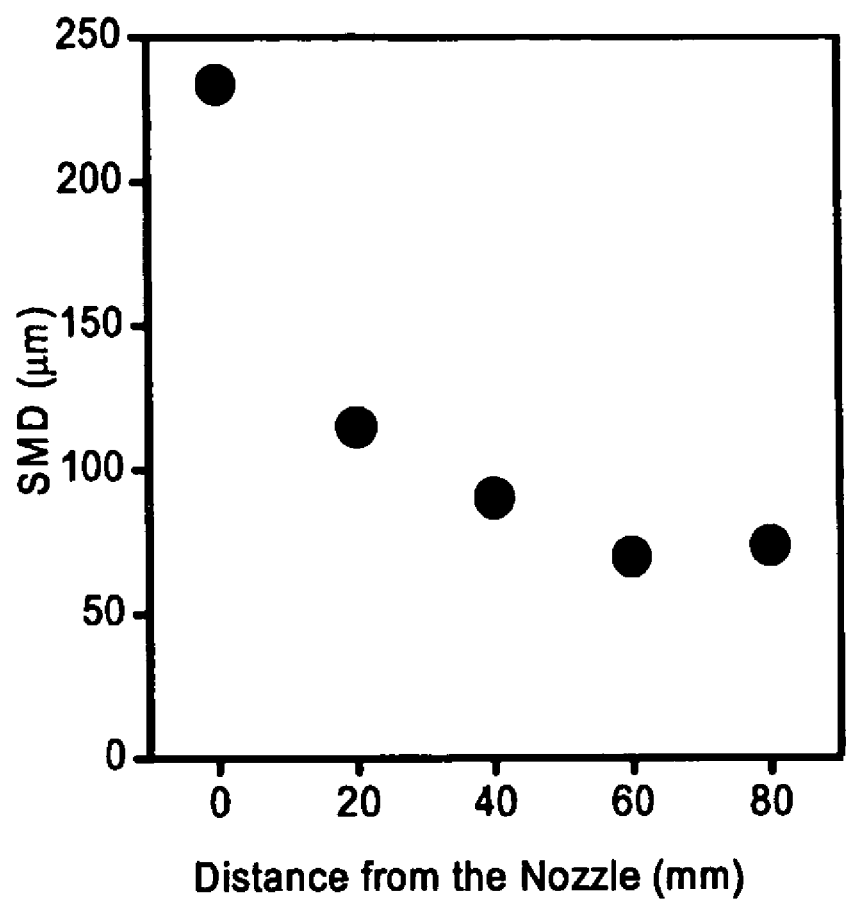
FIG. 15 shows the relationship between the diameter of the water droplets and the distance from the spray position (nozzle)

The photographed images were analyzed and Sauter's mean diameter (SMD) was calculated for the water microdroplets. These results are shown in FIG. 15. The diameter of the water droplets sprayed from the nozzle declined due to evaporation, and, with regard to the size reduction rate, it was confirmed that the water droplets got smaller as a function of the distance from the nozzle. Water droplets were also confirmed in the image taken at the position 220 mm from the nozzle, which confirmed that a portion of the water droplets are present in the heating medium as a liquid.

Example 10

Figure 16:
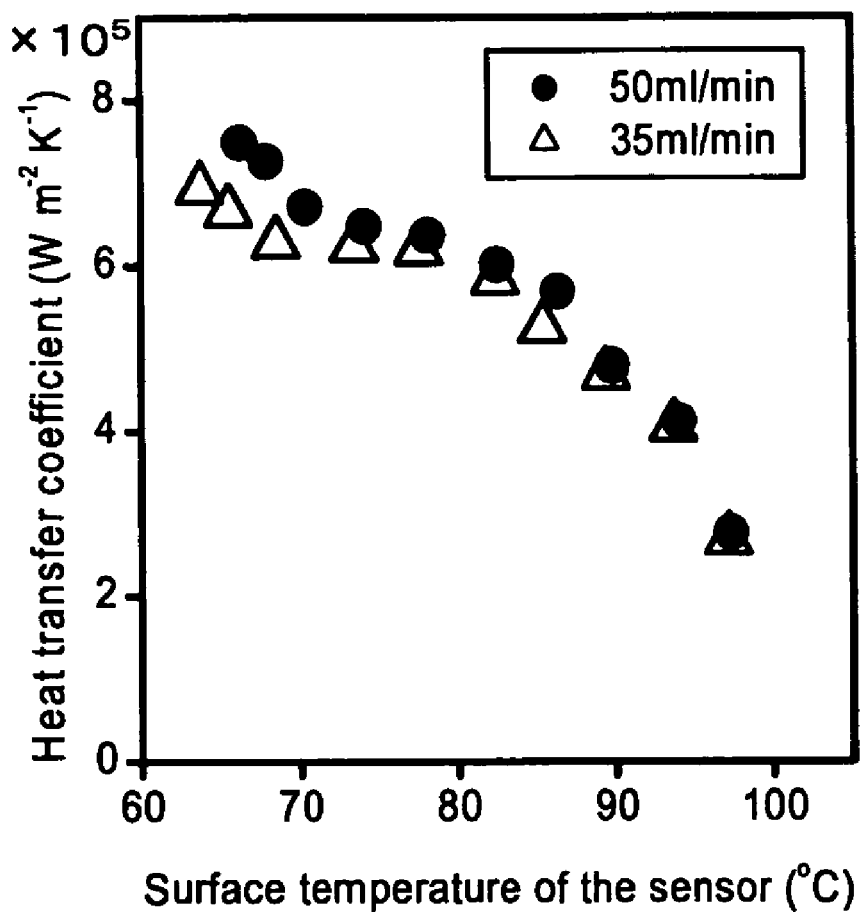
FIG. 16 shows the relationship between the temperature of the surface of the heat flux sensor and the heat transfer coefficient.

The superior nature of the heat transfer properties of Aquagas was examined in this example. The heat flux was measured by placing a heat flux sensor with a temperature-controllable sensor surface in the Aqua-gas and varying the temperature of the sensor surface between 60 to 100° C. In addition, in order to investigate the influence of the quantity of water microdroplets in the Aqua-gas on the heat transfer properties, the heat flux was measured and the heat transfer coefficient was calculated using 35 mL/min and 50 mL/min for the quantity of water sprayed into approximately 180 L superheated steam. The results are shown in FIG. 16.

It was confirmed that the heat transfer coefficient depends on the temperature of the heat transfer surface and on the amount of water microdroplets, and it was thought that this is due to the effect of the water microdroplets on heat transfer. The heat transfer coefficient values reported with the open triangle in the figure are believed to refer to superheated steam due to the smaller amount of water. The values reported with the filled circle are Aqua-gas at ordinary conditions. It is seen that, in the initial heating phase (60 to 70° C.) of a food, the transfer coefficient is high and the heat transfer characteristics are improved by, inter alia, the attachment of the water microdroplets on the surface.

Example 11

Figure 17:
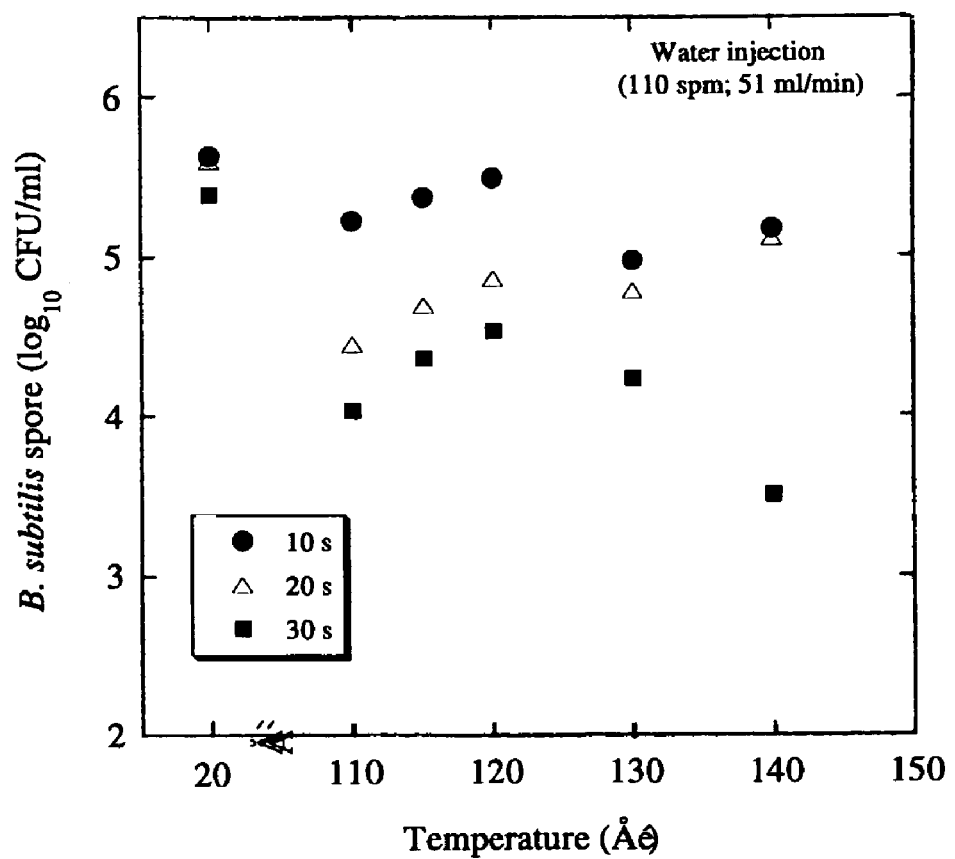
FIG. 17 is an explanatory diagram that shows the pasteurizing effect of Aqua-gas (110° C.).

The superior nature of the heat transfer characteristics of Aqua-gas (pasteurizing effect) was examined in this example. A standard agar medium coated with *B. subtilis* spores ($10^5$ to $10^6$ CFU/plate) was used. Using an Aqua-gas prototype no. 1 device (VT2-7SB), treatment was carried out using different treatment temperatures (110, 115, 120, 130, 140° C.) and different treatment times (0, 10, 20, 30 sec). The amount of water discharged was 51 mL/min (initial device setting). After the treatment, the agar medium was scraped from the Petri dish and placed in a Stomacher bag, 50 mL sterilized physiological saline was added, and grinding and pulverization was carried out for 1 minute in a Stomacher. 10 mL of the agar suspension was heated for 20 minutes at 80° C.; 1 mL of the sample liquid was then taken to a sterilized Petri dish and mixed and diluted with standard agar; cultivation was carried out for 48±3 hours at 37° C.; and the number of colonies produced was then measured. These results are reported in FIG. 17.

The pasteurizing effect was better at longer treatment times. In addition, when the treatment temperature was 110 to 120° C., the pasteurizing effect declined as the temperature rose. It is thought that this was related to the influence of the atmosphere within the chamber (water/steam). According to the figure, when the temperature is increased from 110° C. (Aqua-gas state) to 120° C. or 130° C., the pasteurizing effect declines. This is thought to be due to the following: since the amount of water is constant, the water microdroplets decrease when the temperature is higher, resulting in conversion to a superheated steam atmosphere; this in turn leads to a reduced heat transfer and a diminished pasteurizing effect.

INDUSTRIAL APPLICABILITY

As described in the preceding, the present invention relates to a method and apparatus for heating and pasteurization by means of gaseous water. In accordance with the present invention, heating and pasteurization can be carried out by subjecting a material to be treated to continuous amplitude heating at a temperature difference of at least 10° C. in the temperature range of 90 to 180° C. The interior of the heating chamber for heating the material to be treated while also isolating same from the outside environment, can be substituted by water in gas form and thereby converted into a gas component (gaseous water atmosphere) having a humidity of at least 99.0% and an oxygen concentration no greater than 0.1%. The material to be treated can be heated and pasteurized in a short period of time in a minimally aggressive and highly efficient manner. The present invention can be applied to the thawing of frozen products, to the heating, pasteurization, and cooking of agricultural products and food ingredients, and to the heating, drying, and baking of, for example, wood, metals, and ceramics. The present invention also provides a gaseous water-based heating and pasteurizing apparatus that produces gaseous water and uses it as a heating medium.

The invention claimed is:

1. A method for heating and pasteurizing a material, comprising:
    placing the material inside of a semi-sealed chamber at atmospheric pressure that contains an atmosphere produced by replacing air in the chamber with a gas component produced by spraying or injecting hot water droplets and steam at a temperature of at least 100° C. into the chamber which is heated to a temperature of at least 100° C. which is equal to or higher than the temperature of the sprayed hot water droplets and steam, which gas component has a humidity of at least 95% and contains no more than 1% oxygen;
    contacting said material to the gas component for exposing it to continual temperature variation during heating ranging from 10-50° C. inside the chamber at temperature(s) ranging from 90-180° C. for a time sufficient to heat or pasteurize it.

2. The method of claim 1, wherein said material is frozen.

3. The method of claim 1, wherein said material is an agricultural product or food ingredient.

4. The method of claim 1, wherein said material is wood, metal or ceramic.

5. The method of claim 1, wherein said gas component has a humidity of at least 99%.

6. The method of claim 1, wherein said contacting occurs at a temperature ranging from 95-150° C.

7. The method of claim 1, wherein said mixture of water droplets and steam is continuously injected into the semi-sealed chamber.

8. The method of claim 1, wherein the gas component is a mixture of moist hot steam and water droplets, which are produced by evaporation of hot water droplets sprayed into the semi-sealed chamber that is held at a temperature of at least 100° C.

9. The method of claim 1 that is performed using an apparatus comprising:
    a heating chamber with a semi-sealed configuration that heats said material while isolating it from the outside atmosphere;
    heating means that heats the heating chamber to a prescribed temperature exceeding 100° C.; and
    a steam-generating means that continuously injects hot water heated to at least 100° C. and/or steam into the heating chamber, thereby generating water droplets and steam and transporting same in a prescribed direction, wherein heating or pasteurization are carried out by continuously injecting hot water heated to at least 100° C. and/or steam into the heating chamber, thereby generating hot water droplets and/or steam, and filling the interior of the heating chamber with steam and water droplets such in an atmospheric pressure state, replacing air in the interior of the heating chamber with a gas component that has a composition of at least 95% humidity and an oxygen concentration of not more than 1.0% and that is maintained in a temperature range of 90 to 180° C.

10. The method of claim 1 that is performed using an apparatus comprising as the steam-generating means, a feed water tank, a feed water pump that feeds water from the feed water tank to the heating chamber, a feed water capillary that is provided with an external heater in order to heat the supplied water to at least 100° C., a spray nozzle disposed at the tip of the feed water capillary, and a rotatable circulation fan.

11. The method of claim 1 that is performed using an apparatus comprising:
    a heating means that heats the heating chamber to a prescribed temperature above 100° C. and contains a plurality of sheath heaters disposed in a hairpin configuration in a position in contact with the hot water droplets and steam generated within the heating chamber.

* * * * *